US006368827B1

(12) United States Patent
Tarleton et al.

(10) Patent No.: US 6,368,827 B1
(45) Date of Patent: Apr. 9, 2002

(54) KINETOPLASTID PROTEIN EXPRESSION SYSTEM AND METHODS

(75) Inventors: Rick L. Tarleton, Watikinsville; Nisha Garg, Watkinsville, both of GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/453,322

(22) Filed: Dec. 2, 1999

Related U.S. Application Data

(60) Provisional application No. 60/110,678, filed on Dec. 2, 1998.

(51) Int. Cl.$^7$ .............. C12P 21/06; C12N 1/10; C12N 15/63; C07H 21/04
(52) U.S. Cl. ............... 435/69.1; 435/258.1; 435/320.1; 536/23.1; 536/24.1
(58) Field of Search ............... 435/69.1, 258.1, 435/320.1; 536/23.1, 24.1

(56) References Cited

U.S. PATENT DOCUMENTS

| | | | |
|---|---|---|---|
| 5,665,565 A | 9/1997 | Petri, Jr. et al. | 435/69.1 |
| 5,733,778 A | 3/1998 | Matlashewski et al. | 435/320.1 |
| 5,904,920 A | * 5/1999 | Dranoff et al. | 424/93.21 |
| 5,955,333 A | 9/1999 | Beverley et al. | 435/471 |
| 6,020,144 A | 2/2000 | Gueiros-Filho et al. | 435/7.22 |
| 6,027,934 A | 2/2000 | Powell | 435/320.1 |

OTHER PUBLICATIONS

Hughes et al., "Introduction of Plasmid DNA Into the Trypanosomatid Protozoan *Crithidia fasciculata*," *Proc. Natl. Acad. Sci. USA*, 83(16):6058–6062 (1986).

Tobin et al., "Mutational Analysis of a Signal Sequence Required for Protein Secretion in *Leishmania major*," *Mol. Biochem. Parasitol.*, 62(2)243–249 (1993).

Al–Qahtani et al., "A 5' untranslated region which directs accurate and robust translation by prokaryotic and mammalian ribosomes," *Nuc. Acids Res.*, 24(6):1173–1174 (1996).

Armah et al., "S–Myristoylation of a Glycosylphosphatidylinositol–specific Phospholipase C in *Trypanosoma brucei*," *J. Biol. Chem.*, 274(9):5931–5938 (1999).

Ausubel et al., eds., *Current Protocols in Molecular Biology*, vol. 1–4, John Wiley & Sons, U.S., Title page, publication page and table of contents only, 12 pgs. (1994).

Bellofatto et al., "Stable transformation of *Leptomonas seymouri* by circular extrachromosomal elements," *Proc. Natl. Acad. Sci. USA*, 88:6711–6715 (1991).

Biebinger et al., "A Plasmid Shuttle Vector Bearing an rRNA Promoter is Extrachromosomally Maintained in *Crithidia fasciculata*," *Exp. Parasitol.*, 83:252–258 (1996).

Carpenter et al., "Linearized free maxicircle DNA in *Crithidia fasciculata* is a product of topoisomerase II–mediated cleavage," *Mol. Biochem. Parasitol.*, 76:115–123 (1996).

Clayton et al., "Protein Trafficking in Kinetoplastid Protozoa," *Microbiol. Rev.*, 59(3):325–344 (1995).

Coburn et al., "Stable DNA transfection of a wide range of trypanosomatids," *Mol. Biochem. Parasitol.*, 46:169–179 (1991).

Cross et al., "The Surface Trans–Sialidase Family of *Trypanosoma cruzi*," *Annu. Rev. Microbiol.*, 47:385–411 (1993).

(List continued on next page.)

*Primary Examiner*—Robert A. Schwartzman
*Assistant Examiner*—Katharine F. Davis
(74) *Attorney, Agent, or Firm*—Mueting, Raasch & Gebhardt, P.A.

(57) ABSTRACT

The invention relates to the expression of proteins in non-pathogenic protozoans. In particular, the invention relates to the expression and subsequent isolation of proteins from the nonpathogenic protozoan Crithidia.

42 Claims, 4 Drawing Sheets

Drocourt et al., "Cassettes of the *Streptoalloteichus hindustanus ble* gene for transformation of lower and higher eukaryotes to phleomycin resistance," *Nuc. Acids Res.*, 18(13):4009 (1990).

Englund, "The Structure and Biosynthesis of Glycosyl Phosphatidylinositol Protein Anchors," *Annu. Rev. Biochem.*, 62:121–138 (1993).

Ford et al., "Fusion Tails for the Recovery and Purification of Recombinant Proteins," *Protein Expr. Purif.*, 2, 95–107 (1991).

Freedman et al., "Two more independent selectable markers for stable transfection of Leishmania," *Mol. Biochem. Parasitol.*, 62:37–44 (1993).

Garg et al., "Delivery by *Trypanosoma cruzi* of Proteins into the MHC Class 1 Antigen Processing and Presentation Pathway," *J. Immunol.*, 158:3293–3302 (1997).

Garg et al., "Proteins with Glycosylphosphatidylinositol (GPI) Signal Sequences Have Divergent Fates during a GPI Deficiency," *J. Biol. Chem.*, 272(19):12482–12491 (1997).

Goldring et al., "Stable Transfection in the Monogenetic Trypanosomatid *Leptomonas collosoma*—Transcription Barrier of Heterologous Trypanosomatid SL RNA Genes and Expression of a Chimeric SL RNA Molecular," *Exp. Parasitol.*, 84:28–41 (1996).

Ha et al., "Use of the green fluorescent protein as a marker in transfected Leishmania," *Mol. Biochem. Parasitol.*, 77:57–64 (1996).

Inverso et al., "*Crithidia fasciculata* contains a transcribed leishmanial surface proteinase (gp63) gene homologue," *Mol. Biochem. Parasitol.*, 57:47–54 (1993).

Kaslow, principal investigator, "Recombinant Protein Expression Unit (RPEU)," Abstract, Grant for FY 1997, sponsored by the National Institute of Allergy and Infectious Diseases, National Institutes of Health (Available on–line on or before Apr. 27, 1998).

Kaslow, principal investigator, "Recombinant Protein Expression Unit (RPEU)," Abstract, Grant for future years beyond FY 1997, sponsored by the National Institute of Allergy and Infectious Diseases, National Institutes of Health (Available on–line on or before Apr. 27, 1998).

Kelly, et al., "A shuttle vector which facilitates the expression of transfected genes in *Trypanosoma cruzi* and Leishmania," *Nuc. Acids Res.*, 20(15):3963–3969 (1992).

Kelly, "Trypanosomatid Shuttle Vectors: New Tools for the Functional Dissection of Parasite Genomes," *Parasitol. Today*, 11(12):447–450 (1995).

Kidder et al., "The Growth and Nutrition of *Crithidia fasciculata*," *J. Gen. Microbiol.*, 18:621–638 (1958).

Kozak, "Features in the 5' Non–coding Sequences of Rabbit α and β–Globin mRNAs that Affect Translational Efficiency," *J. Mol. Biol.*, 235:95–110 (1994).

Lacalle et al., "Molecular analysis of the pac gene encoding a puromycin N–acetyl transferase from *Streptomyces alboniger*," *Gene*, 79:375–380 (1989).

La Flamme et al., "Expression of mammilian cytokines by *Trypansoma cruzi* indicates unique signal sequence requirements and processing" *Mol. Biochem. Parasitol.*, 75:25–31 (1995).

La Flamme et al., "*Trypanosoma cruzi*: Expression of Interleukin–2 Utilizing both Supercoiled Plasmids and Linear DNAs," *Exp. Parasitol.*, 83:159–163 (1996).

LeBowitz et al., "Development of a stable Leishmania expression vector and application to the study of parasite surface antigen gene," *Proc. Natl. Acad. Sci. USA*, 87:9736–9740 (1990).

LeBowitz et al., "Simultaneous transient expression assays of the trypanosomatid parasite Leishmania using β–galactosidase and β–glucuronidase as reporter enzymes," *Gene*, 103:119–123 (1991).

McGhee et al., "Biology and Physiology of the Lower Trypanosomatidae," *Microbiol. Rev.*, 44(1):140–173 (1980).

Mensa–Wilmot et al., "A Glycosylphosphatidylinositol (GPI)–Negative Phenotype Produced In *Leishmania major* by GPI Phospholipase C from *Trypanosoma brucei*: Topography of Two GPI Pathways," *J. Cell Biol.*, 124(6):935–947 (1994).

Mensa–Wilmot et al., "Purification and Use of Recombinant Glycosylphosphatidylinositol–Phospholipase C," *Methods Enzymol.*, 250:641–655 (1995).

Rashid et al., "Roles of Gln81 and Cys80 in catalysis by glycosylphosphatidylinositol–phospholipase C from *Trypanosoma brucei*," *Eur. J. Biochem.*, 264:914–920 (1999).

Sambrook et al., *Molecular Cloning, a Laboratory Manual*, Cold Spring Harbor Laboratory Press, Cold Spring Harbor, Mew York, Title page, publication page and table of contents only, 30 pgs. (1989).

Santos et al., "The identification and molecular characterization of *Trypanosoma cruzi* amastigote surface protein–1, a member of the trans–sialidase gene super–family," *Mol. Biochem. Parasitol.*, 86:1–11 (1997).

Schenkman et al., "Mucin–like glycoproteins linked to the membrane by glycosylphosphatidylinositol anchor are the major acceptors of sialic acid in a reaction catalyzed by trans–sialidase in metacyclic forms of *Trypanosoma cruzi*," *Mol. Biochem. Parasitol.*, 59:293–303 (1993).

Seifert et al., "Shuttle mutagenesis: A method of transposon mutagenesis for *Saccharomyces cerevisiae*," *Proc. Natl. Acad. Sci. USA*, 83, 735–739 (1986).

Sheibani, "Prokaryotic Gene Fusion Expression Systems and Their Use in Structural and Functional Studies of Proteins," *Prep. Biochem. Biotechnol.*, 29(1):77–90 (1999).

Swinkels et al., "A phosphoglycerate kinase–related gene conserved between *Trypanosoma brucei* and *Crithidia fasiculata*," *Mol. Biochem. Parasitol.*, 50: 69–78 (1992).

Teilhet et al., "Effect of short 5' UTRs on protein synthesis in two biological kingdoms," *Gene*, 222:91–97 (1998).

Tobin et al., "Transfected Leishmania Expressing Biologically Active IFN–γ," *J. Immunol.*, 150(11):5059–5069 (1993).

Torri et al., "A β–Like DNA Polymerase from the Mitochondrion of the Trypanosomatid *Crithidia fasciculata*," *J. Biol. Chem.*, 269(11):8165–8171 (1994).

Udenfriend et al., "How Glycosylphosphatidylinositol–Anchored Membrane Proteins Are Made," *Annu. Rev. Biochem.*, 64:563–591 (1995).

Ullu et al., "Chapter 7: Trans–splicing in trypanosomatid protozoa," *Molecular Biology of Parasitic Protozoa*, Smith et al., eds., IRL Press, Oxford, Title page, publication page, table of contents, and pp. 115–133 (1996).

Vanhamme et al., "Control of Gene Expression in Trypanosomes," *Microbiol. Rev.*, 59(2):223–240 (1995).

Voth et al., "Differentially expressed *Leishmania major* gp63 genes encode cell surface leishmanolysin with distinct signals for glycosylphosphatidylinositol attachment," *Mol. Biochem. Parasitol.*, 93:31–41 (1998).

Wallace "Flagellate Parasites of Mosquitoes with Special Reference to *Crithidia fasciculata* Léger, 1902," *J. Parasitol.*, 29:196–205 (1943).

Wirtz et al., "Inducible Gene Expression in Trypanosomes Mediated by a Prokaryotic Repressor," *Science*, 268:1179–1183 (1995).

Wirtz et al., "Regulated processive transcription of chromatin by T7 RNA polymerase in *Trypanosoma brucei*," *Nuc. Acids Res.*, 26(20):4626–4634 (1998).

Wirtz et al., "A tightly regulated inducible expression system for conditional gene knock-outs and dominant-negative genetics in *Trypanosoma brucei*," *Mol. Biochem. Parasitol.*, 99:89–101 (1999).

Zhang et al., "The expression of biologically active human p53 in Leishmania cells: a novel eukaryotic system to produce recombinant proteins," *Nuc. Acids Res.*, 23(20):4073–4080 (1995).

Zhang et al., "Identification and overexpression of the A2 amastigote-specific protein in *Leishmania donovani*," *Mol. Biochem. Parasitol.*, 78:79–90 (1996).

Zhang et al., "Loss of virulence in *Leishmania donovani* deficient in an amastigote-specific protein, A2," *Proc. Natl. Acad. Sci. USA*, 94:8807–8811 (1997).

Korman et al. Proc. Natl. Acad. Sci. USA 84:2150–2154 Apr. 1987.*

McCarvey et al. Biotechnology 13:1484–1487 1995.*

Cruz et al., Gene replacement in parasitic protozoa, Nature 348: 171–173, Nov. 1990.*

* cited by examiner

SEQUENCE LISTING

<160> NUMBER OF SEQ ID NOS: 14

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
aagcttagga ggttttacc atggaagacg ccaaaaac                    38

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
cgtacgtgat gttcacctcg a                                     21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
ctgttctata ttgtagcggc ca                                    22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
ttatgacctt gcggtttcct t                                     21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
actagtaccg aagcttagga gggtt                                 25

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6

```
actagtagtt acctataacct gattttatt                                         29

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
taagaacgtt ttccataact taggaggcag atcatgattg aacaagatgg a               51

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
tatgaacgtt ttcttagaag aactcgtcaa gaag                                  34

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
taaggatcct taacacagga ggcagaccat gtttggtggt gtaaag                     46

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
taaggatcct tatgaccttg cggtttcctt                                       30

<210> SEQ ID NO 11
<211> LENGTH: 47
<212> TYPE: PRT
<213> ORGANISM: Trypanosoma cruzi

<400> SEQUENCE: 11

Met Phe Ser Lys Arg Thr Ser Pro Ala Pro Phe Arg Ala Leu Leu Leu
  1               5                  10                  15

Pro Val Val Val Val Val Val Val Ala Ser Val Ala Leu Pro
             20                  25                  30

Ala Gly Ala Gln Phe Asp Leu Arg Gln Gln Gln Leu Val Ile Gln
         35                  40                  45

<210> SEQ ID NO 12
<211> LENGTH: 18
<212> TYPE: PRT
<213> ORGANISM: Influenza

<400> SEQUENCE: 12
```

```
Met Ala Ile Ile Tyr Leu Ile Leu Leu Phe Thr Ala Val Arg Gly Asp
 1               5                  10                  15

Pro Asp

<210> SEQ ID NO 13
<211> LENGTH: 22
<212> TYPE: PRT
<213> ORGANISM: Mus musculus

<400> SEQUENCE: 13

Met Tyr Ser Met Gln Leu Ala Ser Cys Val Thr Leu Thr Leu Val Leu
 1               5                  10                  15

Leu Val Asn Ser Ala Pro
            20

<210> SEQ ID NO 14
<211> LENGTH: 48
<212> TYPE: PRT
<213> ORGANISM: Trypanosoma cruzi

<400> SEQUENCE: 14

Val Thr Asn Ser Phe Leu Tyr Asn Arg Pro Leu Ser Glu Asp Glu Leu
 1               5                  10                  15

Lys Met Val Lys Lys Glu Asp Ser Val Arg Gly Asp Val Ser Arg
            20                  25                  30

Val Leu Pro Leu Leu Leu Leu Gly Leu Trp Gly Leu Thr Gly Leu Tyr
            35                  40                  45
```

US 6,368,827 B1

KINETOPLASTID PROTEIN EXPRESSION SYSTEM AND METHODS

CONTINUING APPLICATION DATA

This application claims the priority of U.S. Provisional Application Serial No. 60/110,678, filed Dec. 2, 1998, Expired which is incorporated by reference herein.

BACKGROUND OF THE INVENTION

Efficient and high-level heterologous expression of proteins is an important alternative to the isolation of protein from native sources and is especially useful when the native protein is normally produced in limited amounts or by sources which are impossible, expensive and/or dangerous to obtain or propagate. Although a number of expression systems have proven useful for production of various heterologous proteins, none of these systems is universally applicable for the production of all proteins. For instance, *E. coli* lacks the ability to provide many post-translational modifications to heterologous proteins. Yeast can provide some of these post-translational modifications, but rapid degradation of heterologous proteins is common and secretion of heterologous proteins with long, untrimmed oligosaccharide chains sometimes results in biologically inactive or antigenically altered proteins. Moreover, a replacement of the natural mammalian signal peptide with a yeast signal peptide is almost always required for efficient secretion of mammalian proteins by yeast. Expression of heterologous eukaryotic proteins in insect or mammalian cells are good alternatives but both require rather expensive medium for cell propagation. Moreover, yeast, cultured insect cells and mammalian cells all have a long doubling time.

Protozoans represent an alternative for the expression of heterologous proteins, however only pathogenic protozoans have been characterized to the extent necessary for routine heterologous protein expression. Well-characterized pathogenic protozoans include *Trypanosoma cruzi, Trypanosoma brucei*, and *Leishmania* spp. A number of shuttle vectors designed for episomal replication (i.e., integrated into the chromosome and replicating independently of nuclear replication) and coding region expression in pathogenic protozoans have been developed. An inducible coding region expression system has been established for pathogenic *T. brucei* (Wirtz, E., et al., *Science*, 268, 1179–1183 (1995)). Vectors that allow efficient coding region expression in different hosts like *E. coli* and mammalian cells have also been developed (Al-Qahtani, A., et al., *Nucleic Acids Res.*, 24 1173–1174 (1996)). It was recently determined that mammalian and protozoan signal peptides function in *T. cruzi* to target proteins to different cellular compartments (Garg, N. et al., *J. Immunol.*, 158, 3293–3302 (1997)). Also, bioactive cytokines (IL-2 and IFN-gamma) have been produced in both *T. cruzi* and *Leishmania* (La Flamme, A. C., et al., *Mol. Biochem. Parasitol.*, 75, 25–31 (1995), and Tobin, J. F., et al., *J. Immunol.*, 150 5059–5069 (1993)), suggesting that mammalian signal peptides are recognized and processed by these protozoans. However, pathogenic protozoans have not been exploited as a general purpose protein expression system, presumably because they are difficult or expensive to grow in large numbers and/or are infectious to human beings.

There have been unsuccessful attempts to use the nonpathogenic protozoan Crithidia to express heterologous proteins. In one study, Crithidia was transfected with vectors that contained a putative rRNA promoter and one of three reporter coding regions encoding luciferase, chloramphenicol acetyltransferase or β-galactosidase (Biebinger et al., *Exp. Parasitol.*, 83, 252–258 (1996)). The reporter coding regions were inserted between a 5'-trans splicing signal and a 3'-untranslated region isolated from the Crithidia phosphoglycerate kinase coding region. This 5'-trans splicing signal had previously been shown to function in *T. brucei*. However, despite using regulatory regions endogenous to Crithidia, no activity of the reporter was detected in transient expression assays. When coding regions encoding resistance to hygromycin or G418 were used instead of the reporter coding regions, drug resistant cells were obtained, but at low efficiency. There was no evidence that integration of any of the vectors into genomic DNA had occurred.

In another study, shuttle vectors designed for episomal replication and coding region expression in *Leishmania* spp. (Coburn, C. M., et al., *Mol. Biochem. Parasitol.*, 46, 169–179 (1991)) were introduced into Crithidia. The vectors were stably maintained in Crithidia at a copy number higher than occurred in Leishmania. However, in Crithidia the level of the protein encoded by the coding regions present on the vectors were significantly lower than the levels expressed in Leishmania.

A protein expression system that provides for the efficient expression and isolation of correctly post-ranslationally modified heterologous proteins in a nonpathogenic host would constitute a much desired advance in the art.

SUMMARY OF THE INVENTION

The invention provides a method for producing a polypeptide that involves providing a host cell containing a vector that includes a 5' regulatory region, a 3' regulatory region, and a coding region encoding a polypeptide Blocated therebetween, then culturing the host cell under conditions that allow expression of the coding region such that the polypeptide encoded by the coding region is produced. The coding region is operably linked to the 5' regulatory region and the 3' regulatory region, and the host cell is a nonpathogenic protozoan. The nonpathogenic protozoan can be a member of the order Kinetoplastida, including the nonpathogenic protozoan Crithidia. The 5' regulatory region and the 3' regulatory region can be derived from a protozoan, including a Leishmania HMTX$^r$ 5' or 3' regulatory region, a Leishmania DHFR 5' or 3' regulatory region, or a Leishmania A2 5' or 3' regulatory region. Optionally, the polypeptide can be isolated.

The vector used in the method can further include a second 5' regulatory region, a second 3' regulatory region, and a second coding region located therebetween. The second coding region encodes a detectable marker and is operably linked to the second 5' regulatory region and the second 3' regulatory region. The second 5' regulatory region and the second 3' regulatory region can be derived from a protozoan, including a Leishmania HMTX$^r$ 5' or 3' regulatory region, a Leishmania DHFR 5' or 3' regulatory region, or a Leishmania A2 5' or 3' regulatory region. The detectable marker can be a selectable marker that encodes resistance to a drug.

The polypeptide encoded by the first coding region can include an amino terminal signal peptide, for instance amino acids 1–47 (SEQ ID NO:11) of the *T. cruzi* glycoprotein gp-72, amino acids 1–18 (SEQ ID NO:12) of influenza hemagglutinin, or amino acids 1–22 (SEQ ID NO:13) of murine interleukin-2. The polypeptide encoded by the first coding region can include a GPI cleavage/attachment site, for instance amino acids 632–679 (SEQ ID NO:14) of amastigote surface protein I.

The vector used in the methods can be a plasmid that is maintained either extrachromosomally in the nonpathogenic protozoan host cell or integrated into the genomic DNA of the nonpathogenic protozoan host cell. Further, the vector useful in the method of the invention is also encompassed within the scope of the invention.

The invention also provides a nonpathogenic protozoan that contains a vector of the invention. The nonpathogenic protozoan can be a member of the order Kinetoplastida, including the nonpathogenic protozoan Crithidia.

ABBREVIATIONS USED IN THE FIGURES

Figure 1:
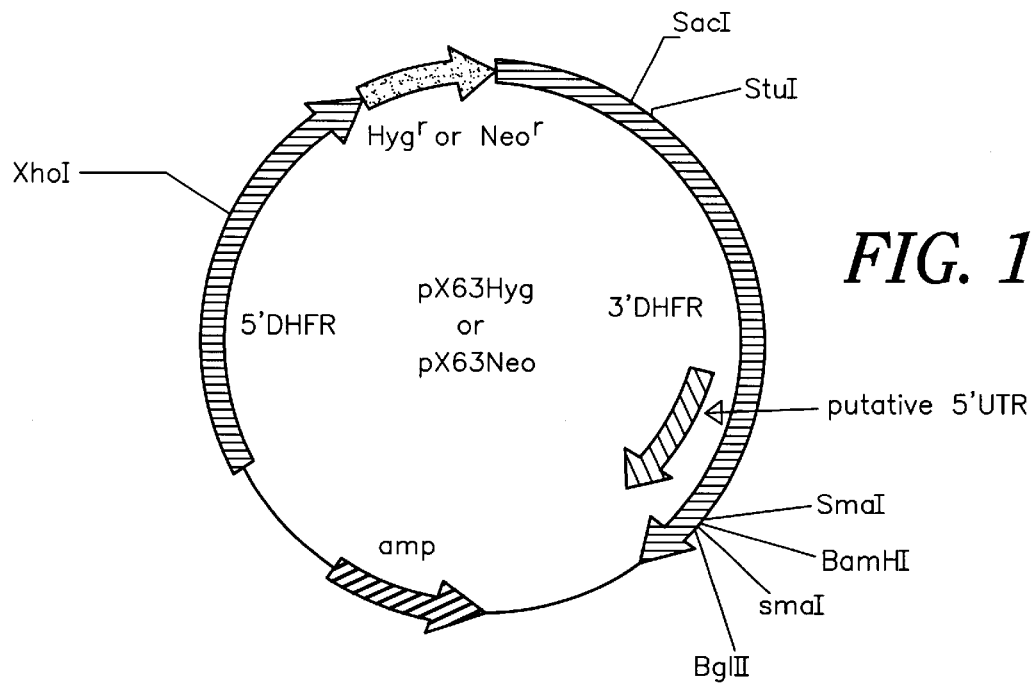
FIG. 1 depicts the expression vectors pX63.Hyg and pX63.Neo

HPH, HPT, Hyg, and Hyg$^r$, coding region encoding hygromycin-B-phosphotransferase (provides hygromycin resistance); Neo$^r$, coding region encoding neo-aminoglycoside phosphotransferase (provides neomycin and G418 resistance); 5'hmtx$^r$, and 5'MTX, 5' regulatory region and splice acceptor site from *Leishmania major* H region methotrexate resistance gene (HMTX$^r$); 3'hmtx$^r$, and 3'MTX, 3' regulatory region from *L. major* HMTX$^r$; 5'DHFR, 5' regulatory region and splice acceptor site from *L. major* dihydrofolate reductase gene (DHFR); 3'DHFR, 3' regulatory region from *L. major* DHFR; amp, gene encoding β-lactamase and conferring ampicillin resistance; Luc, luciferase coding region; pyt, 92 base pair synthetic pyrimidine tract; A2 5' UTR, 5' regulatory region of the *L. donovani* A2 gene; A2 3' UTR, 3' regulatory region of the *L. donovani* A2 gene.

DETAILED DESCRIPTION

The present invention provides methods for producing polypeptides, and vectors useful in the methods. Vectors useful in the invention contain a coding region that encodes a polypeptide to be produced in a nonpathogenic protozoan. A vector can provide for further cloning (amplification of the DNA), i.e., a cloning vector, or for expression of the polypeptide encoded by the coding region, i.e., an expression vector. The term vector includes but is not limited to plasmid, viral, cosmid and episomal vectors. Preferably, the vector can replicate autonomously, i.e., extrachromosomally, which can allow for high numbers of the vector to be maintained and potentially results in higher protein production. Vectors are preferably circular, but can be linear. Construction of suitable vectors employs standard ligation techniques known in the art. See, e.g., Sambrook et al, *Molecular Cloning: A Laboratory Manual*, Cold Spring Harbor Laboratory Press (1989) or Ausubel, R. M., ed. *Current Protocols in Molecular Biology* (1994).

"Coding region," "coding sequence," and "open reading frame" are used interchangeably and refer to a region of nucleic acid that can be transcribed and/or translated into a polypeptide, typically when placed under the control of the appropriate regulatory regions. A coding region can contain introns and exons. Preferably a coding region contains no introns. A coding region can be derived from genomic DNA of an organism, or from a cDNA produced using the mRNA of an organism.

Replicable cloning and expression vectors generally contain one or more of the following: an origin of replication, regulatory regions, and a coding region. An origin of replication allows for the replication of the vector in a nonpathogenic protozoan. Origins of replication that function in prokaryotic organisms are also useful in protozoans; thus typically no special origin of replication is needed for replication in the nonpathogenic protozoans of the invention. Conveniently, the vectors useful in the present invention are preferably able to replicate in prokaryotes, a prokaryotic host cell such as *E. coli* can be used during construction of the vector. Vectors capable of replication in both prokaryotes and eukaryotes are known in the art as "shuttle" vectors.

As used herein, the term "regulatory region" refers to a nucleotide sequence that contains regulatory elements and is operably linked to a coding region. A coding region is "operably linked" to a regulatory region when the regulatory region affects or regulates the transcription and/or the translation of that coding region. A coding region that is "operably linked" to a regulatory region includes, for example, an appropriate start signal (e.g., ATG) at the beginning of the nucleic acid sequence to be expressed and a reading frame that permits expression of the coding region under control of the regulatory region to yield production of the encoded polypeptide. A coding region that is "operably linked" to a regulatory region can also include a termination sequence, such as a codon for which there is no corresponding aminoacetyl-tRNA, thus ending peptide synthesis.

"Regulatory elements" are recognized by the processing enzymes of a host cell and play a role in affecting and/or regulating coding region expression, including, for instance, transcription, translation, and/or mRNA stability. In DNA, regulatory regions and the regulatory elements present therein are typically present 5' and 3' of a coding region that is to be expressed. An example of a regulatory element in DNA is a transcription initiation site. In contrast to most other biological systems, e.g., bacteria or mammalian cells, classical promoters do not appear to be necessary for coding region expression in kinetoplastid protozoans, thus it is optional but typically not required that a coding region in a kinetoplastid protozoan be operably linked to a classical promoter.

In mRNA, regulatory regions and the regulatory elements present therein are typically present in the untranslated regions (UTRs), i.e., 5' and 3' of the coding region that is to be translated. Regulatory elements within the regulatory regions of an mRNA can include a signal for the addition of a precapped oligoribonucleotide, also referred to as a miniexon or splice leader, to the 5' end of the mRNA. The miniexon originates from the processing of a miniexon donor RNA that is typically transcribed on arrays of repeated coding regions and supplied in trans. The signal to add a splice leader to the 5' end of the mRNA is known to the art as splice acceptor site (SAS) and is present 5' of a coding region. Regulatory regions can also include a signal for the polyadenyation of the 3' end of the mRNA. This signal is known to the art as a polyadenylation site and is generally present 3' of a coding region. Another regulatory region that can be present is an intergenic polypyrimidine tract. An example of a polypyrimidine tract is pyt. This is a 92 base pair synthetic pyrimidine tract that can provide the trans-splicing site and ensure correct polyadenylation at the 3' end of a transcript (Zhang, W. W. et al., *Proc. Natl. Acad. Sci. USA*, 94, 8807–8811 (1997)). Other regulatory elements of an mRNA can be those that enhance the translation of the coding region present on the mRNA. Regulatory regions that enhance translation include a ribosome binding site, a spacer between the ribosome binding site and the translation start site, and/or translation enhancer sequences. These types of regulatory regions are preferably located immediately 5' of the coding region. Examples of regulatory regions that can be used to enhance translation includes the Ner RBS-hybrid spacer disclosed in Al-Qahtani et al (*Nucleic Acids Res.*, 24, 1173–1174, (1996)), and the LacZRBS-spacer-TES spacer disclosed in Teilhet et al., *Gene*, 222, 91–97 (1998).

Preferred regulatory regions are flanking regulatory regions derived from protozoa, i.e., nucleotides that are present upstream and downstream of a protozoan coding region. Nonlimiting examples of flanking regulatory regions that can be used in the practice of the invention include those associated with the Leishmania DHFR gene (available at GenBank Accession Nos. Y00124, which contains the 5' regulatory region, and X51733, which contains the 3' regulatory region), the Leishmania $HMTX^r$ gene (available at GenBank Accession No. L01699), and the *Leishmania donovani* A2 gene (Zhang, W. W. et al., *Mol. Biochem. Parasitol.*, 78, 79–90 (1996), Zhang, W. W. et al., *Proc. Natl. Acad. Sci. USA*, 94, 8807–8811 (1997); U.S. Pat. No. 5,733,778, Matlashewski et al.). Preferably, the regulatory regions are those associated with the Leishmania $HMTX^r$ gene.

When a coding region to be inserted into a vector of the present invention is not originally isolated from a protozoan, e.g., the coding region is isolated from a human or is synthesized, the coding region is operably linked during construction of the vector to regulatory regions that are recognized by a nonpathogenic protozoan. For instance, the regulatory regions can be ligated to the coding region prior to insertion of the coding region into the vector. Alternatively and preferably, the vector contains regulatory regions and the coding region is inserted in the proper orientation between the 5' and 3' regulatory regions. Optionally, as detailed in the Examples, the regulatory regions that are present in the vector have a multiple cloning region (MCR) between the 5' and 3' regulatory regions. This provides for the insertion of a coding region into a vector in a way that operably links it to the regulatory regions.

When the coding region to be inserted into a vector of the present invention is isolated from a protozoan, the protozoan coding region may already be operably linked to regulatory regions that function in a nonpathogenic protozoan. For instance, when the coding region is isolated as genomic DNA, regulatory regions may already be operably linked to the coding region. When the coding region is isolated as a cDNA, the regions 5' and 3' of the coding region may contain regulatory regions. The wild-type regulatory regions operably linked to the protozoan coding region can be used, or the regulatory regions can be removed and replaced with other regulatory regions, including those associated with, e.g., the Leishmania $HMTX^r$ gene, the Leishmania DHFR gene and the Leishmania A2 gene.

A vector useful in the invention preferably contains at least one coding region which is operably linked to 5' and 3' regulatory regions (also referred to as the "flanking regulatory regions"). Typically, the 5' and 3' regulatory regions are from the same gene. For instance, a 5' $HMTX^r$ regulatory region and a 3' $HMTX^r$ regulatory region can be operably linked to a coding region. Optionally, the two regulatory regions operably linked to a coding region are not from the same gene. For instance, a 5' $HMTX^r$ regulatory region and a 3' DHFR regulatory region can be operably linked to a coding region.

More preferably, the vector includes at least two coding regions, each of which is operably linked to separate 5' and 3' flanking regulatory regions. In this aspect of the invention, typically one coding region will encode a detectable marker and the second coding region will encode the polypeptide that is to be produced and/or isolated. The at least two coding regions can be present in a vector in any order.

In one embodiment of the vector that includes at least two coding regions, the first flanking regulatory regions operably linked to a first coding region and the second flanking regulatory regions operably linked to a second coding region are the same. For instance, first 5' $HMTX^r$ and 3' $HMTX^r$ regulatory regions can be operably linked to a first coding region, and second 5' $HMTX^r$ and 3' $HMTX^r$ regulatory regions can be operably linked to a second coding region. In another embodiment of the vector, first flanking regulatory regions operably linked to a first coding region and second regulatory regions operably linked to a second coding region are different. For instance, first 5' $HMTX^r$ and 3' $HMTX^r$ regulatory regions can be operably linked to a first coding region, and second 5' DHFR and 3' DHFR regulatory regions can be operably linked to a second coding region. Preferably, the first flanking regulatory regions operably linked to a first coding region and the second flanking regulatory regions operably linked to a second coding region are the same. Optionally, a spanning region can be present between the first regulatory regions and the second regulatory regions. A spanning increases the number of nucleotides between the first and second coding regions. Typically, a spanning region is at least about 18 base pairs, preferably about 1000 base pairs, more preferably greater than about 1000 base pairs.

Optionally, a 5' or 3' regulatory region derived from a protozoan is minimized or shortened, provided that nucleotides necessary for affecting and/or regulating expression of a coding region (i.e., the regulatory elements) are not removed. Generally, shortening a regulatory region involves the removal of one or more nucleotide sequences from the regulatory region while leaving the signals required for processing, for instance the splice acceptor site or the polyadenylation site, undisturbed. Methods to shorten regulatory regions include, for instance, the use of preexisting restriction endonuclease sites to remove portions of a regulatory region, or the use of PCR to introduce restriction endonuclease sites into a regulatory region. For instance, about 1.5 kilobases (kb) of the 5' region of the $HMTX^r$ 5' regulatory region can be removed without altering its function. Another example is the removal of about 3.4 kb of the 3' region of the $HMTX^r$ 3' regulatory region, which can likewise be effected without altering its function. Shortening regulatory regions is useful as it decreases the overall size of the vector and thereby can make introduction of the vector to nonpathogenic protozoan cells more efficient.

Optionally, circular vectors can be used that provide for integration of at least a portion of the vector into the genomic DNA of a nonpathogenic protozoan. The term "genomic DNA" refers to DNA normally present in an organism, i.e., all DNA present prior to introduction of a heterologous coding region. "Genomic DNA" includes nuclear DNA, including chromosomal DNA, and extranuclear DNA, including kinetoplast DNA. Integrated plasmids do not require drug selection, and thus typically provide stable and efficient expression of the heterologous polypeptide encoded by the integrated vector. Preferably, vectors are integrated into the genomic DNA at a specific site. Integration of a vector at a specific site can be accomplished by including specific nucleotide sequences in the vector. Preferably the specific nucleotide sequences are identical to nucleotide sequences present in the genomic DNA of the nonpathogenic protozoan. Preferably, there are at least about 50, more preferably at least about 100, and most preferably at least about 200 consecutive nucleotides present in the vector that are also present in the genomic DNA of the nonpathogenic protozoan. For instance, a vector, preferably a plasmid, can contain nucleotide sequences that are identical to either the actin or β-tubulin gene of the nonpathogenic protozoan into which the plasmid is to be introduced. Insertion of this type of vector typically occurs by homologous recombination between the vector and the genomic DNA. A single cross-over event results in the integration of the entire vector into the genomic DNA of the host cell.

Alternatively, a vector that is useful for integration of a nucleotide sequence into the genomic DNA of the host cell into genomic DNA is linear. The nucleotide sequence that is to be integrated is flanked on either side by specific nucleotide sequences that are also present in the genomic DNA of the host cell. Preferably, there are at least about 50, more preferably at least about 100, and most preferably at least about 200 consecutive nucleotides on each side of the nucleotide sequence that is to be integrated into the genomic DNA. Preferably, the vector contains a portion of the actin or β-tubulin gene of the nonpathogenic protozoan into which the plasmid is to be introduced. While not intending to be limiting, a vector typically integrates into the genome of a nonpathogenic protozoan by homologous recombination. Insertion of this type of vector typically occurs by two cross-over events that result in the integration of the nucleotide sequence that is to be integrated.

The coding region of a protein that is to be produced can contain nucleotides that encode a tag to facilitate subsequent isolation of the protein. Several tags are well-known in the art (Ford et al., *Protein Expr. Purif*, 2, 95–107 (1991); Sheibani, *Prep. Biochem. Biotechnol.*, 29,77–90 (1999)). Nonlimiting examples of tags that can be used in the invention include HA (available from Clontech, Palo Alto, Calif.), FLAG (available from Sigma Chemical, St. Louis, Mo.), His (available from Novagen, Madison, Wis.), GST (available from Stratagene, La Jolla, Calif.), and c-myc (available from Invitrogen, Carlsbad, Calif.). A coding region present on a vector of the present invention can also include nucleotides encoding a signal peptide, including, for example, a GPI cleavage/attachment site. Signal peptides are described herein.

Preferably a detectable marker encoded by a coding region is a selectable detectable marker. Nonlimiting examples of selection criteria that can be used in nonpathogenic protozoa include resistance to hygromycin (mediated by the HTH coding region product hygromycin-B-phosphotransferase, hygromycin resistance is also referred to as Hyg resistance, or $Hyg^r$), resistance to G418, (mediated by the $Neo^r$ coding region product neo-aminoglycoside phosphotransferase), resistance to phleomycin (mediated by the *Streptoalloteichus hindustanus* ble coding region product bleomycin resistance protein (BRP), which inhibits phleomycin); resistance to puromycin (mediated by the pac coding region product puromycin N-acetyl transferase), resistance to tunicamycin (mediated by the protein N-acetylglucosamine-1-phosphate transferase), and resistance to streptothricin.

Convenient procedures to introduce a vector into a nonpathogenic protozoan, including microprojectile bombardment or microinjection, can be used in the present invention. Vectors can also be incorporated into liposomes for introduction to nonpathogenic protozoans. Preferably, a vector is introduced into a nonpathogenic protozoan by electroporation. The invention is not intended to be limited by the method of introducing the vector into the host cell, as protozoans pose no particular problems in this regard.

The present invention provides methods for producing eukaryotic and prokaryotic proteins. The methods of the invention uses a nonpathogenic protozoan host cell for the production of eukaryotic and prokaryotic polypeptides. Preferred nonpathogenic protozoans are those of the phylum Protozoa. More preferably a nonpathogenic protozoan belongs to the order Kinetoplastida, most preferably of the family Trypanosomatidae. Members of the Kinetoplastida order are referred to herein as kinetoplastids. Members of the Trypanosomatidae family are referred to herein as trypanosomatids. Examples of kinetoplastids include nonpathogenic members of the genus Trypanosoma, e.g. *Trypanosoma rangeli, Trypanosoma musculi, Trypanosoma mega* (ATCC Number: 30038) and *Trypanosoma neveulemaire* (ATCC Number: 30641); nonpathogenic members of the genus Leishmania, e.g. *Leishmania chamaelonis* and *Leishmania tarentolae*; members of the genus Blastocrithidia, e.g. *Blastocrithidia culicis* (ATCC Number: 30268); members of the genus Herpetomonas, e.g. *Herpetomonas muscarum* (ATCC Number: 30260); members of the genus Leptomonas, e.g. *Leptomonas seymouri* (ATCC Number: 30220); and members of the genus Phytomonas, e.g. *Phytomonas davidi* (ATCC Number: 30287). Preferably, members of the genus Crithidia, e.g. *Crithidia fasciculata*, are used in the methods disclosed herein. An example of a strain of Crithidia that can be used in the present invention is *Crithidia fasciculata* Leger (ATCC Number: 11745).

Nonpathogenic protozoans have several advantages over available biological expression systems. For example, these protozoans have fast growth rates and generally are easy and inexpensive to grow in large numbers. However, until this invention, attempts to use Crithidia or other nonpathogenic protozoans to express a coding region at a level required for efficient isolation of the polypeptide encoded by the coding region were not successful. Typically, the amount of polypeptide expressed by a biological expression system is measured by determining the milligrams of polypeptide produced per liter of culture. Preferably, the polypeptide is produced at a level of at least about 0.05 mg/liter, more preferably about 0.1 mg/liter, most preferably about 1 mg/liter.

In the pharmaceutical and biotechnology industry it is standard practice to test multiple expression systems to empirically determine which one is optimal for each individual protein. Aspects of the present invention can be used in place of or as an adjunct to other protein expression systems for production of proteins needed for the discovery, evaluation, or production of diagnostics, vaccines, therapeutics or medical treatments.

Nonpathogenic protozoans can be used in the methods of the present invention to produce heterologous polypeptides or to overproduce endogenous polypeptides. "Heterologous polypeptide" and "foreign polypeptide" refer to the polypeptide encoded by a heterologous coding region. The terms "heterologous coding region" and "foreign coding region," used interchangeably herein, refer to a coding region that was not originally isolated from the nonpathogenic protozoan into which it is introduced. The term "polypeptide" as used herein, refers to a polymer of amino acids connected by peptide bonds and does not connote a specific length of a polymer of amino acids. Thus, for example, the terms peptide, oligopeptide, protein, and enzyme are included within the definition of polypeptide, whether produced using recombinant techniques, or naturally occurring. The protein expression system may be particularly useful for the production of proteins from related protozoans since the machinery and signals for transcription, translation and post-translational modification in this class of organisms are expected to be evolutionarily conserved.

An "isolated" polypeptide is one that is removed, by whatever means, from the nonpathogenic protozoan that produced the polypeptide. Preferably, the polypeptide is purified, i.e., essentially free from other polypeptides and associated cellular products or other impurities. The method includes causing expression of the coding region, then optionally isolating the polypeptide product of the coding region, i.e., the protein or a fragment thereof. Preferably the polypeptide is biologically active. The polypeptide produced can be a heterologous polypeptide or a polypeptide endogenous to the nonpathogenic protozoan. Preferably, the polypeptide is a heterologous polypeptide.

A polypeptide that is encoded by a coding region and produced according to the method of the invention can be present in the cytoplasm of a nonpathogenic protozoan host cell. However, it can be difficult to isolate a protein from other proteins present in the cytoplasm. Advantageously, the polypeptide can be engineered according to the present invention to include amino acid sequences that influence the final destination of the protein, targeting it to a particular compartment inside the cell or, alternatively, outside the cell. For instance, the protein can include amino acids that encode a signal peptide. Signal peptides, typically a continuous stretch of amino acids, can be located at the amino terminal end or the carboxy terminal end of a polypeptide. An amino terminal signal peptide can direct the polypeptide to which it is attached into the endoplasmic reticulum, other intracellular compartments or to the extracellular space. Different types of signal peptides are used to specify different destinations in the cell. Preferably, if an amino terminal signal peptide is used, the amino terminal signal peptide directs the protein to the endoplasmic reticulum of the nonpathogenic protozoan for eventual secretion and/or attachment to the surface of the nonpathogenic protozoan. Typically, an amino terminal signal peptide is removed from the protein by a specific cleavage event prior to secretion. Nucleotide sequences encoding many signal peptides are well known to the art and can be linked to a coding region so that the nucleotides encoding a signal peptide and the nucleotides comprising a coding region are contiguous and in the same reading frame. Linking can be accomplished by ligation at convenient restriction endonuclease sites. Alternatively, if appropriate sites do not exist synthetic oligonucleotide adaptors or linkers can be used in accord with conventional practice. Many amino terminal and carboxy terminal signal peptides are known to the art, and they are expected to work in the present invention. For instance, the amino terminal signal peptide in the following proteins can be used: variant surface glycoprotein of *T. brucei*, GP63 of Leishmania (Voth et al., *Mol. Biochem. Parasitol.*, 93, 31–41 (1998)), and mucins and trans-sialidases of *T. cruzi* (Schenkman et al., *Mol. Biochem. Parasitol.*, 59, 293 (1993), Cross et al., *Ann. Rev. Microbiol.*, 47, 385–411 (1993)), and the Crithidia gp63 protein (Inverso et al., *Mol. Biochem. Parasitol.*, 57, 47–54 (1993). Other nonlimiting examples of amino terminal signal peptides that can be used in the present invention include amino acids 1–47 of *T. cruzi* glycoprotein gp-72 (MFSKRTSPAPFRALLLPVVVVVVVVVASVALPAGA-QFDLRQQQLVIQ (SEQ ID NO:11), available at Genbank Accession No. M65021), and amino acids 1–18 influenza hemagglutinin (MAIIYLILLFTAVRGDPD (SEQ ID NO:12), as described in Garg, N. et al., *J. Immunol.*, 158 3293–3302 (1997)). Mammalian signal sequences attached to their native proteins do not appear to require modification for secretion in protozoans. Another example is amino acids 1–22 of murine interleukin-2 (MYSMQLASCVTLTLV-LLVNSAP (SEQ ID NO:13), available at Genbank Accession No. K02292). However, the protozoan *T. cruzi* processes the murine IL-2 signal sequence differently than does mouse cells, i.e., the native IL-2 signal sequence is 20 amino acids long when the IL-2 gene is expressed in mouse cells, and 26 amino acids long when expressed in *T. cruzi* (LaFlamme, et al. *Mol. Biochem. Parasitol.*, 75, 25 (1995)).

Preferably, a protein that is encoded by a coding region includes amino acids that encode a glycosylphosphatidylinositol (GPI) cleavage/attachment site. A GPI cleavage/attachment site is a common means of anchoring membrane proteins to eukaryotic cells. A GPI cleavage/attachment site is a C-terminal hydrophobic region that varies considerably in size and sequence among different proteins (see, e.g., Udenfriend et al. *Annu. Rev. Biochem.*, 64 563–591 (1995), and Englund, P., *Annu. Rev. Biochem.*, 62:121–138 (1993)). In size, the C-terminal region is generally between about 17 and about 31 amino acids and includes an approximately 17 residue hydrophobic domain. Many GPI cleavage/attachment sites are known to the art, and they are expected to work in the present invention. For instance, the GPI cleavage/attachment site in the following proteins can be used: variant surface glycoprotein of *T. brucei*, GP63 of Leishmania (Voth et al., *Mol. Biochem. Parasitol.*, 93, 31–41 (1998)), and mucins and trans-sialidases of *T. cruzi* (Schenkman et al., *Mol. Biochem. Parasitol.*, 59 293 (1993), Cross et al., *Ann. Rev. Microbiol.*, 47 385–411(1993)), the Crithidia gp63 protein (Iverso et al., *Mol. Biochem. Parasitol.*, 57, 47–54 (1993), and amino acids 632–679 of amastigote surface protein I (Santos, et al., *Mol. Biochem. Parasitol.*, 86, 1–11 (1997)) (VTNSFLYNRPLSEDELK-MVKKKEDSVRGDVSRVLPLLLLGLWGLTGLY (SEQ ID NO:14), available at Genbank Accession No. U74494).

The presence of a GPI cleavage/attachment site on a protein provides a site for the addition of a GPI anchor to the protein. A common GPI anchor includes ethanolamine phosphate, mannose, glucosamine and inositolphospholipid. This minimal GPI structure can vary between species and can vary between different stages of a species, and can be modified through the remodeling of lipids or the addition of ethanolamines or sugars on mannose residues. Addition of a GPI anchor to a GPI cleavage/attachment site results in a protein that is anchored to the outer surface of the nonpathogenic protozoan.

A protein that is linked to the cell by a GPI anchor is present on the exterior surface of the cell. Generally, the carboxy terminal hydrophobic tail and usually the signal peptide as well are cleaved during transport of the protein to the outer surface of the cell. The GPI anchor binding a protein to the cell surface can be readily cleaved by use of phospholipases. Thus, the use of phospholipase treatment of cells expressing a desired GPI anchored protein on the cell surface is an especially attractive option for protein isolation. For example, glycosylphosphatidylinositol phospholipase C or phosphatidylinositol-specific phospholipase C can be used to cleave the GPI anchor. These enzymes are available from, for instance, Boehringer Mannheim (Indianapolis, Ind.). Generally, cleavage of a GPI anchor causes the release into the surrounding media of the protein that is bound to the cell by the GPI anchor. A protein that contains a GPI cleavage/attachment site preferably also contains an amino terminal signal peptide.

Coding regions introduced into nonpathogenic protozoans can be expressed constitutively. However, constitutive expression may prevent the use of the present invention to produce proteins that are toxic to nonpathogenic protozoa. Preferably, when it is desirable to produce a protein that is toxic to a nonpathogenic protozoan, the expression of the coding region that encodes the protein is controlled. For instance, expression of the coding region can be activated or induced by the presence of transcription factors that bind to a regulatory region and activate expression of the coding region. Likewise, the expression of the coding region can be repressed by the presence of transcription factors that bind to a regulatory region and repress expression of the coding region.

An example of a repressible system includes linking a nucleotide sequence encoding a tetracycline operator to the region 5' of the coding region that encodes the toxic protein. The tetracycline operator is a regulatory region to which a repressor protein, the tetracycline repressor, binds and prevents expression of the coding region to which the operator is operably linked. In those aspects of the invention where a 5' regulatory region includes a splice acceptor site, the tetracycline operator is located between the splice acceptor site and the coding region. In those aspects of the invention where nucleotide sequences that increase the efficiency of translation, e.g., a ribosome binding site and spacer, are operably linked to the coding region, preferably the tetracycline operator sequences are 5' to the a ribosome binding site and spacer. The nonpathogenic protozoa of this aspect of the invention thus also contain a coding region that encodes the tetracycline repressor protein, which binds to the tetracycline operator and represses expression of an operably linked coding region. The coding region that encodes the tetracycline repressor protein can be present on the same vector that encodes the toxic protein, or on a different vector. The tetracycline repressor protein can be removed from the operator by the addition of tetracycline or a tetracycline analog to the nonpathogenic protozoan. Removal of the tetracycline repressor from the operator results in expression of the operably linked coding region.

Typically, a polypeptide produced using the methods of the present invention is isolated. Initially, isolation of a polypeptide present in the cytoplasm of a host cell typically requires lysis of the nonpathogenic protozoan followed by centrifugation to remove cell debris. Cells displaying GPI-anchored proteins includes an initial step of treatment with a phospholipase to cleave the GPI anchor. Preferably the phospholipase is glycosylphosphatidylinositol phospholipase C or phosphatidylinositol-specific phospholipase C. For instance, a nonpathogenic protozoan expressing a protein attached to the outer surface of the cell by a GPI anchor can be grown in bulk, washed to remove contaminating media components, and treated with a phospholipase to obtain isolated protein. Likewise, secreted polypeptides can be isolated by centrifugation.

Once polypeptides have been separated from cell debris, the polypeptide of interest can be further purified using purification methods that are well known in the art. The following are nonlimiting examples of suitable protein purification procedures: fractionation on immunoaffinity or ion-exchange columns; ethanol precipitation; reverse phase HPLC; chromatography on silica or on an ion-exchange resin such as DEAE; chromatofocusing; SDS-PAGE; ammonium sulfate precipitation; gel filtration using, for example, Sephadex G-75; and ligand affinity chromatography.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXAMPLE 1

Selection and Design of Coding Region Expression Plasmids for Expression of Foreign Polypeptides in Crithidia The kinetoplastids make polycistronic messenger RNAs that are post transcriptionally processed by trans-splicing of a splice leader RNA at the 5' end followed by polyadenylation at 3' end. The 5' and 3' regulatory regions flanking the structural gene in trypanosomes provides the signal for processing and maturation of transcripts, and expression of proteins. Several shuttle vectors designed for expression of proteins in the trypanosomatids Crithidia, *T. cruzi*, Leishmania, and *T. brucei* were used to test the compatibility of these plasmids in Crithidia based upon the expression of a detectable marker encoded by the plasmid. Several plasmids resulted in significant expression of the detectable marker. Surprisingly, two plasmids originally constructed for high level expression of introduced coding regions in Crithidia did not result in significant expression of the detectable marker.

Materials and Methods

Cells

Crithidia, ATCC No. No. 11745, used for these studies was cultured at 28° C. in Hogellate medium (Kidder et al., *J. Gen. Microbiol.*, 18, 621–638 (1958)). Epimastigotes of *T. cruzi* (Brazil strain) were cultured at 28° C. in liver infusion tryptose (LIT) medium (Garg et al., *J. Immunol.*, 158, 3293–3302 (1997)) supplemented with 5% heat-inactivated fetal bovine serum (HyClone, Logan, Utah).

Vectors and vector construction

Plasmid construction was done using techniques know to the art (see, for instance, Sambrook et al, *Molecular Cloning: A Laboratory Manual.*, Cold Spring Harbor Laboratory Press (1989)). *E. coli* was used as the host for the construction of the plasmids.

The plasmids pX63.Hyg and pX63.Neo (FIG. 1) were provided by Dr. S. Beverley (Washington University, St. Louis, Mo.). pX63.Hyg is described in U.S. Pat. No. 5,955,333 (Beverley et al.). These plasmids contain an Hyg$^r$ or Neo$^r$ gene, respectively, flanked by *L. major* DHFR 5' and 3' regulatory regions. The terms DHFR and DHFR-TS are used interchangeably herein.

Figure 2:
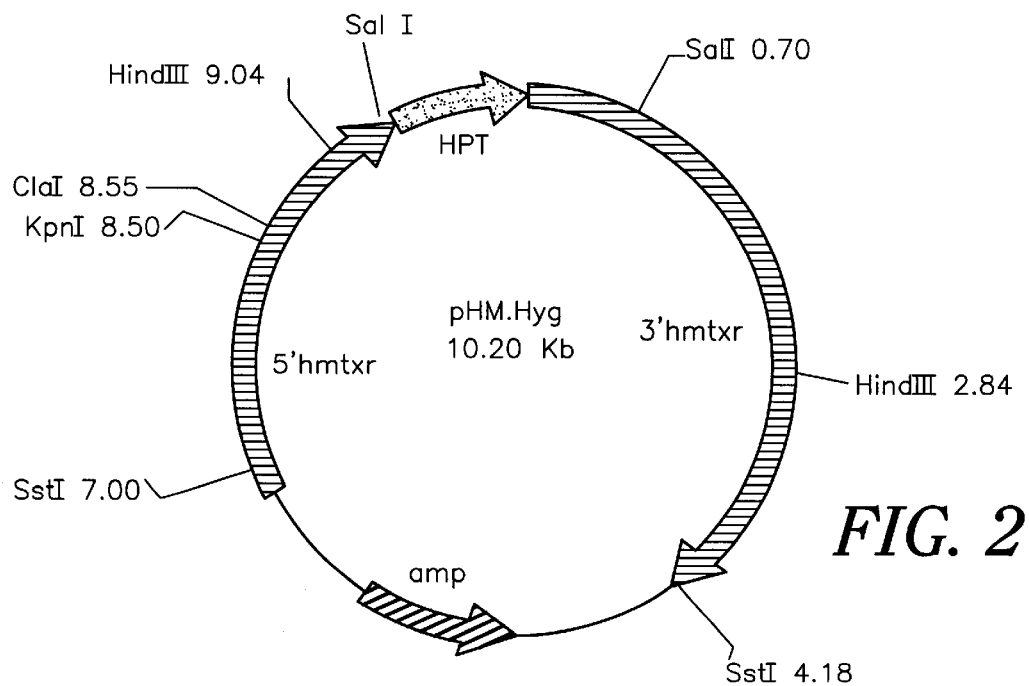
FIG. 2 depicts the expression vector pHM.Hyg
Figure 3:
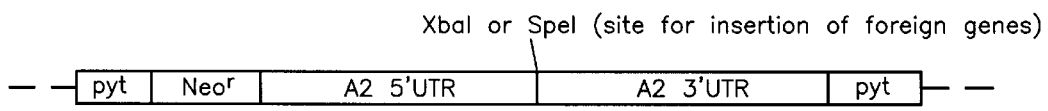
FIG. 3 depicts the expression vector pSP72neo

The plasmid pXneo was provided by Dr. S. Beverley. This plasmid contains a Neo$^r$ gene flanked by DHFR 5' and 3' regulatory regions.

pHM.Hyg (FIG. 2) was provided by Dr. S. Beverley (Washington University). This plasmid contains the HMTX$^r$ regulatory regions flanking the HPT gene.

pSP72neo (FIG. 3) and pKSneo were provided by Dr. Mat Yamage (NIH). This plasmid contains the A2 regulatory regions flanking a cloning site.

Transfection

Plasmid DNAs for transfection were prepared by the alkaline lysis method. For transfection, late log phase culture of cells was harvested, washed in ice-cold PBS and suspended in electroporation buffer (2.7 mM KCl, 1.7 mM $KH_2PO_4$, 8 mM $K_2HPO_4$, 137 mM NaCl, 0.5 mM Mg acetate, 0.1 mM $CaCl_2$) at $1 \times 10^8$ cells/ml. Cell suspensions ($4 \times 10^7$, 400 µl) were incubated in 0.2 cm electroporation cuvettes with plasmid DNA (25 µg) on ice for 10 minutes and electroporated using a Bio-Rad Gene Pulser. Crithidia was pulsed twice at 500 µF, 400 V, while *T. cruzi* epimastigotes were transfected with plasmid DNA and pulsed three times at 960 µF, 300 V. Following 48 hours of incubation at 28° C. without selection, Crithidia was cultured in Hogellate liquid media in the presence of G418 (2.5–100 µg/ml) or hygromycin (2.5–1500 µg/ml) to select stable transformants. *T. cruzi* epimastigotes were cultured in media containing 100–800 µg/ml of G418 or 100–1500 µg/ml hygromycin.

Results

In general, the ability of these plasmids to provide for stable protein production in Crithidia was tested by electroporating the plasmids into Crithidia in log phase growth, and selecting for resistance to the appropriate drug, either G418 or hygromycin. Drug resistance was indicated by the survival and growth of Crithidia and growth at higher concentrations of drug was suggestive of better expression of the drug resistance coding region, and consequently, more efficient protein expression provided by the plasmid.

All the Leishmania shuttle vectors (i.e., pX63.Hyg, pX63.Neo, pHM.Hyg, pX.Hyg, pMTX.Hyg, pXHyg.MTXLuc, pSP72neo, pSP72neo.Luc, pX.Neo, pXNeo.XGFP, pUTK, and pUTK.GPIPLC) were capable of providing the expression of drug resistance genes in Crithidia (Tables 1, 2). Based upon the shuttle vector used, a variable degree of resistance to hygromycin or G418 was obtained in Crithidia transfectants (Table 2). Crithidia cells transfected with pHM.Hyg containing 5' and 3' regulatory regions of $HMTX^r$ locus of Leishmania exhibited the highest expression of the $Hyg^r$ gene as determined by the level of hygromycin resistance (Table 2). In comparison, vectors containing 5' and 3' regulatory regions of *T. brucei* and *T. cruzi* genes were not expressed in Crithidia (Table 3). It was not possible to establish drug resistant lines of Crithidia transfected with the episomal expression vectors listed in Table 3.

TABLE 1

Shuttle vectors that have been used for the expression of foreign proteins in *C. fasciculata*

| | Plasmid | Flanking Sequences | Drug Resistance | Marker Gene | Reference |
|---|---|---|---|---|---|
| 1. | pX63.Hyg | DHFR-TS | $Hyg^r$ | None | LeBowitz et al., 1991 |
| 2. | pX63.Neo | " | $Neo^r$ | " | LeBowitz et al., 1991 |
| 3. | pX63Hyg.GPIPLC | " | $Hyg^r$ | GPI-PLC | Mensa-Wilmot et al., 1997 |
| 4. | pHM.Hyg | $HMTX^r$ | $Hyg^r$ | " | Freedman & Beverley, 1993 |
| 5. | pHM.Hyg.GPIPLC | " | " | GPI-PLC | |
| 6. | pX.Hyg | DHFR | " | None | |
| 7. | pMTX.Hyg. | $HMTX^r$ | " | " | |
| 8. | pXHyg.MTXLuc | DHFR, $HMTX^r$ | " | Luc | |
| 9. | pSP72neo | A2 | $Neo^r$ | None | Matlashewski et al., 1997 |
| 10. | pSP72neo.Luc | " | " | Luc | |
| 11. | pX.Neo | DHFR | " | None | Das et al., 1996 |
| 12. | pXNeo.XGFP | " | " | GFP | |
| 13. | pUTK | " | Kan/Neo | None | |
| 14. | pUTK.GPIPLC | " | Kan/Neo | GPI-PLC* | |

Abbreviations: DHFR-TS, Dihydrofolate reductase-thymidylate synthase; GPI-PLC*, Inactive glycosylphosphatidylinositol phospholipase C protein; HMTX, H region-methotrexate resistance gene; A2, A2 locus expressed in amastigotes of Leishmania; $Neo^r$, Neomycin resistance gene; $Hyg^r$, Hygromycin resistance gene; GFP, Green fluorescent protein; Kan, kanamycin resistance gene.
Cited documents: Mensa-Wilmot, et al. J. Cell. Biol., 124, 935–947 (1994); LeBowitz et al., Gene, 103, 119–123 (1991); Freedman & Beverley, Mol. Biochem. Parasitol., 62, 37–44 (1993); Zhang et al., Proc. Natl. Acad. Sci. USA, 94, 8807–8811 (1997); Ha et al., Mol. Biochem. Parasitol., 77, 57–64 (1996).

TABLE 2

Shuttle vectors that have been used for the expression of foreign proteins in *C. fasciculata*

| | | | Drug Concentration (µg/ml) | | | | | | |
|---|---|---|---|---|---|---|---|---|---|
| | Plasmid | Drug | 0 | 10 | 25 | 50 | 100 | 200 | 500 |
| 1. | pX63.Hyg | Hyg | +++ | ++ | ++ | ++ | ++ | ND | ND |
| 2. | pX63.Neo | Neo | +++ | + | ++ | − | − | ND | ND |
| 3. | pX63Hyg.GPIPLC | Hyg | +++ | − | − | − | ND | ND | ND |
| 4. | pHM.Hyg | Hyg | +++ | +++ | +++ | +++ | +++ | +++ | +++ |
| 5. | pHM.Hyg.GPIPLC | " | +++ | − | − | ND | ND | ND | ND |
| 6. | pX.Hyg | " | +++ | +++ | +++ | +++ | ++ | ND | ND |
| 7. | pMTX.Hyg. | " | +++ | +++ | +++ | +++ | +++ | +++ | +++ |

TABLE 2-continued

Shuttle vectors that have been used for the expression of foreign proteins in C. fasciculata

| | | | Drug Concentration (μg/ml) | | | | | | |
|---|---|---|---|---|---|---|---|---|---|
| | Plasmid | Drug | 0 | 10 | 25 | 50 | 100 | 200 | 500 |
| 8. | pXHyg.MTXLuc | " | +++ | +++ | +++ | +++ | + | ND | ND |
| 9. | pSP72neo | Neo | +++ | +++ | +++ | +++ | + | ND | ND |
| 10. | pSP72neo.Luc | " | +++ | +++ | +++ | +++ | + | ND | ND |
| 11. | pX.Neo | " | +++ | ++ | ++ | ++ | ++ | + | ND |
| 12. | pXNeo.XGFP | " | +++ | + | ++ | ++ | ++ | + | ND |
| 13. | pUTK | " | +++ | +++ | +++ | +++ | +++ | +++ | ND |
| 14. | pUTK.GPIPLC* | " | +++ | +++ | +++ | +++ | +++ | +++ | ND |

Abbreviations used: ND, Not determined; +++, logarithmic replication; ++, Replication at a slower rate; +, Surviving but not replicating; −, Cell death.

TABLE 3

Vectors that do not provide the expression of foreign proteins in C. fasciculata

| | Plasmid | Derived For | Flanking Sequences | Drug Resistance | Marker Gene | Reference |
|---|---|---|---|---|---|---|
| 1. | pHD214 | C. fasciculata | PGK | None | Luciferase | Biebinger & Clayton, 1996 |
| 2. | pHD299 | " | " | Hyg | None | Biebinger & Clayton, 1996 |
| 3. | pHD328 | T. brucei | Actin | " | None | |
| 4. | pHD421 | " | Actin and aldolase | " | Luciferase | |
| 5. | pTEX.Neo | T. cruzi | GAPDH | Neo | None | Kelly et al., 1992 |
| 6. | pTEX.Hyg | " | " | Hyg | None | |
| 7. | pTEX.Hyg.GPIPLC | " | " | " | GPI-PLC | |

Abbreviations: GAPDH, glyceraldehyde phosphate dehydrogenase; GPI-PLC, glycosylphosphatidylinositol phospholipase C; PGK, phosphoglycerate kinase.
Cited documents: Biebinger et al., Exp. Parasitol., 83, 252–258 (1996); Kelly et al., Nucl. Acids Res., 20, 3963–3969 (1992).

These results identify the Leishmania genes (HMTX$^r$, DHFR and A2) whose 5' and 3' regulatory regions were capable of providing the signal for processing and maturation of transcripts and constitutive expression of drug resistance genes in Crithidia.

The 5' and 3' regulatory regions of Leishmania but not all the kinetoplastid genes are recognized by the Crithidia transcription/translation machinery. This suggests a degree of specificity of the RNA processing and protein translation system in Crithidia. The results also show that the Neo$^r$ and Hyg$^r$ genes can be used as drug selection markers in Crithidia.

Considering that the level of hygromycin or G418 resistance is directly related to the rate of expression of Hyg$^r$ and Neo$^r$ genes, respectively, the 5' and 3' regulatory regions of the HMTX$^r$ locus of Leishmania provide more efficient transcription and translation in Crithidia than any other 5' and 3' regulatory regions tested.

EXAMPLE 2

Expression of a Foreign Gene Along with a Selection Marker

This example demonstrates modification of the plasmids conferring drug resistance to express foreign genes along with the drug resistance genes. Regulation of coding region expression in protozoans is largely achieved post-transcriptionally by modulating the rates of trans-splicing and poly-adenylation, the rates of degradation of pre-mRNA and mRNA, and the rate of export of mRNA from the nucleus (Ullu, E., et al., In *Molecular Biology of Parasitic Protozoa*. D. F. Smith and M. Parson, ed. IRL Press, p. 115–133 (1996)). In trypanosomatids, the 5' and 3' sequences flanking the coding region often play a role in post-transcriptional regulation. Polycistronic messenger RNAs are post-transcriptionally processed by trans-splicing of a splice leader RNA at the 5' end (also referred to as a miniexon) followed by polyadenylation at the 3' end (Ullu, E., et al., In *Molecular Biology of Parasitic Protozoa*. D. F. Smith and M. Parson, ed. IRL Press, p. 115–133 (1996)). For instance, in Leishmania, transcription of the hygromycin coding region present in pHM.Hyg is controlled by 5' and 3' flanking sequences of the constitutively expressed Leishmania HMTX$^r$ coding region.

For the efficient transcription in a nonpathogenic protozoan of a selectable marker as well as a coding region of interest, inserted coding regions should be associated by their own 5' and 3' regulatory regions. However, some regulatory regions may not be recognized by Crithidia. Thus the efficiency of expression of heterologous coding regions will vary.

The coding regions of interest chosen were luciferase, GPI-PLC, and GFP. The decision to express these genes was based upon the availability of easy and sensitive enzyme and/or antibody assays for the detection of GPI-PLC, luciferase, and GFP.

Materials and Methods

Cells and transfection

The cells and transfections were done as described in Example 1.

Figure 5:
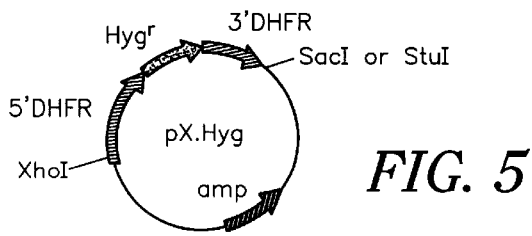
FIG. 5 depicts the expression vector pX.Hyg
Figure 6:
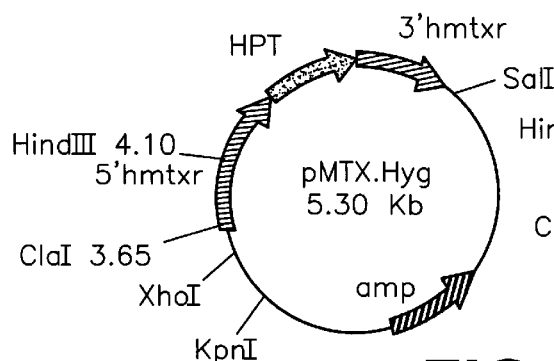
FIG. 6 depicts the expression vector pMTX.Hyg

Vector construction pX.Hyg (FIG. 5) (also known as pBS-DH.Hyg) was derived from pX63.Hyg. The flanking DHFR regulatory regions in pX63Hyg were reduced in size to make pXHyg. This was accomplished by digesting pX63.Hyg with either XhoI/StuI or XhoI/SacI to yield a 2.3 kb fragment. This 2.3 kb was cloned in pBSK (Stratagene, La Jolla, Calif.) at the XhoI/EcoRV or XhoI/SacI sites to yield pXHyg. pXHyg contained the full length 1.1 kilobase $Hyg^r$ gene flanked by 0.5 kilobases of the 5' DHFR regulatory region and 0.8 kilobases of the 3' DHFR regulatory region.

pMTX.Hyg (FIG. 6, also known as pBS-HM.Hyg) was derived from pHM.Hyg. First, pHM.Hyg was digested with KpnI/SalI, and 0.52 kilobases 5' regulatory region of HMTX was cloned in pBSK at KpnI/SalI sites. The resulting plasmid was pBSK.0.52 5'MTX regulatory region. Next, 1.9 kb SalI fragment from pHM.Hyg (containing $Hyg^r$ gene and about 0.8 kilobases of the 3'MTX regulatory region) was isolated. This fragment was cloned in pBSK.0.52 5'MTX regulatory region at SalI site to construct pMTX.Hyg.

Figure 7:
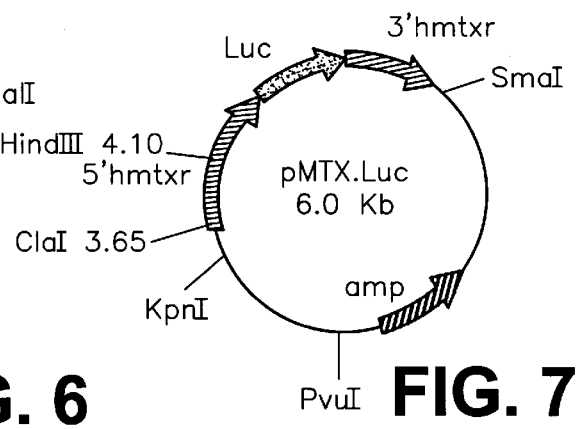
FIG. 7 depicts the expression vector pMTX.Luc

The plasmid pX63Hyg.GPIPLC was provided by Dr. Mensa-Wilmot (University of Georgia). This plasmid contains the cDNA encoding the *T. brucei* GPIPLC gene (available at GenBank Accession No. M27301) cloned in pX63.Hyg at the BglII site. Since the cDNA was used, the post-transcriptional modifications that occur to the mRNA from which this cDNA is derived were present.

pMTX.Luc (FIG. 7) was made such that a luc gene was flanked by $HMTX^r$ regulatory regions. First, a luc gene containing an upstream translation enhancer was constructed by modifying the luc gene present in pHD421 (Wirtz et al., *Mol. Biochem. Parasitol.*, 99, 89–101 (1999); Wirtz et al., *Nucl. Acids Res.*, 26, 4626–4634 (1998)). The 5' upstream translation enhancer was added by amplifying the luc gene present in pHD421 with the primer pair 5' <u>AAGCTTAGG</u>AGGTTTTTACC<u>ATG</u>GAAGACGCCAAAAAC (SEQ ID NO:1) and 5' <u>CGTACG</u>TGATGTTCACCTCGA (SEQ ID NO:2). SEQ ID NO:1 contains a HindIII site (underlined nucleotides) and a nerACC upstream translation enhancer, and nucleotides of the 5' region of the luc coding region (double underlined nucleotides). SEQ ID NO:2 contains a BsiWI site (underlined nucleotides). The amplified fragment was about 160 base pairs in length, and was ligated to pHD421 at the HindIII/BsiWI sites to result in pHD421.nerluc. The luc gene (1.8 kb) from pHD421.nerluc was isolated by digestion of pHD421.nerluc with HindIII/BamHI. The fragment was subcloned in the pBSK.0.52 5'MTX regulatory region (described above) that had been digested with HindIII/BamHI. The resulting plasmid was designated pBSK0.52 1luc. Next, 0.8 kilobase 3' $HMTX^r$ regulatory region from pMTX.Hyg was isolated by ScaI/NotI digestion and subcloned into pBSKO.521luc at BamHI (blunt ended)/NotI sites to result in pMTX.Luc.

Figure 8:
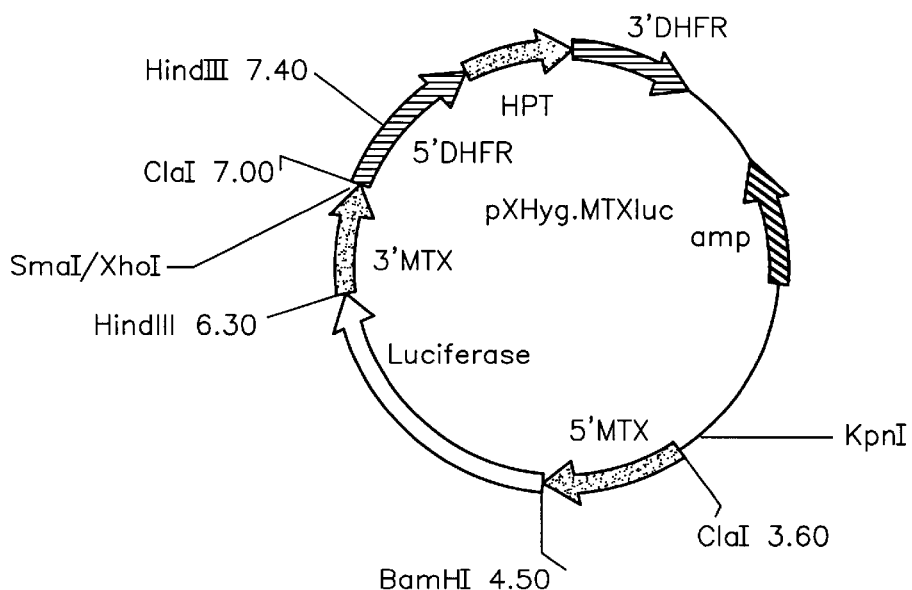
FIG. 8 depicts the expression vector pXHyg.MTXLuc

To construct pHMHyg.GPIPLC, a *T. brucei* cDNA encoding GPIPLC was amplified by PCR using pTEX.GPIPLC (Garg, N. et al., *J. Biol. Chem.*, 272, 12482–12491 (1997)) as template. The primers used for the amplification were 5' C.TGTTCTATATTGTAGCGGCCA (SEQ ID NO:3), and 5' TTATGACCTTGCGGTTTCCTT (SEQ ID NO:4). The amplified product was exposed to dATP in the presence of Taq polymerase to add A overhangs. The amplified PCR product with A overhangs was cloned in pHM.Hyg (T) vector. To make pHM.Hyg T vector, pHM.Hyg was digested with Kpn I, followed by T4 polymerase treatment to fill in the single stranded overhangs. Next, the linear, blunt-ended plasmid was treated with Taq polymerase in the presence of dTTP that resulted in addition of T overhangs. The resulting plasmid was pHMHyg.GPIPLC.

pXHyg.MTX.luc (FIG. 8) was constructed by sub-cloning of a 3.1 kilobase region made up of the luc gene flanked by the 5' $HMTX^r$ regulatory region and the 3' regulatory region from pMTX.Luc (FIG. 7) into pXHyg (FIG. 5). pMTX.Luc was digested with KpnI, SmaI and PvuI. The 3.1 kb fragment (released by SmaI/KpnI digestions) was purified and subcloned in pX.Hyg at XhoI (blunt ended)/KpnI site. The resulting plasmid pXHyg.MTX.luc contained luc gene flanked by the 5' $HMTX^r$ regulatory region and the 3' $HMTX^r$ regulatory region followed by $Hyg^r$ gene flanked by the 5' DHFR regulatory region and the 3' DHFR regulatory region. The 3' $HMTX^r$ regulatory region and the 5' DHFR regulatory region in this plasmid were separated by ~18 base pairs. These ~18 base pairs were provided by restriction sites present in the multiple cloning sites.

To construct pSP72neo.luc or pKSneo.luc, a 1.8 kb luc gene was amplified by PCR using pHD421.nerluc as template. The primers used for the amplification were 5'ACTAGTACCGAAGCTTAGGAGGGTT (SEQ ID NO:5), and 5' ACTAGTAGTTACCTATACCTGATTTTATT (SEQ ID NO:6). Oligonucleotides for PCR amplification were designed to incorporate SpeI sites at 5' and 3' ends. "A" overhangs were added to the amplified product as described above. The PCR amplified 1.8 kb nerluc product was first cloned in pTOPO.T vector (Invitrogen, Carlsbad, Calif.) at the T overhangs present in the vector. The luc gene was then subcloned from pTOPO.luc by digestion with XbaI and ligated to pSP72neo that had been digested with XbaI. The resulting plasmid was designated pSP72neo.luc. The luc gene was also subcloned from pTOPO.luc by digestion with XbaI and ligated to pKSneo that had been digested with SpeI. The resulting plasmid was designated pKSneo.luc.

The pXneo.XGFP plasmid was made by cloning of GFP gene (Invitrogen) into pXneo plasmid such that both $Neo^r$ and GFP gene were flanked by DHFR locus derived 5' and 3' regulatory regions. The nucleotide sequences encoding GFP were isolated from p565T-CL (Invitrogen) by digestion with NheI and EcoRV, blunt ended, and then subcloned into the SmaI site of pX63.Hyg. The 0.8 kilobase 3' regulatory region was cloned at the BglII site. This 3' regulatory region was derived by BspEI and BclI digestion of pX63.Hyg.

Figure 9:
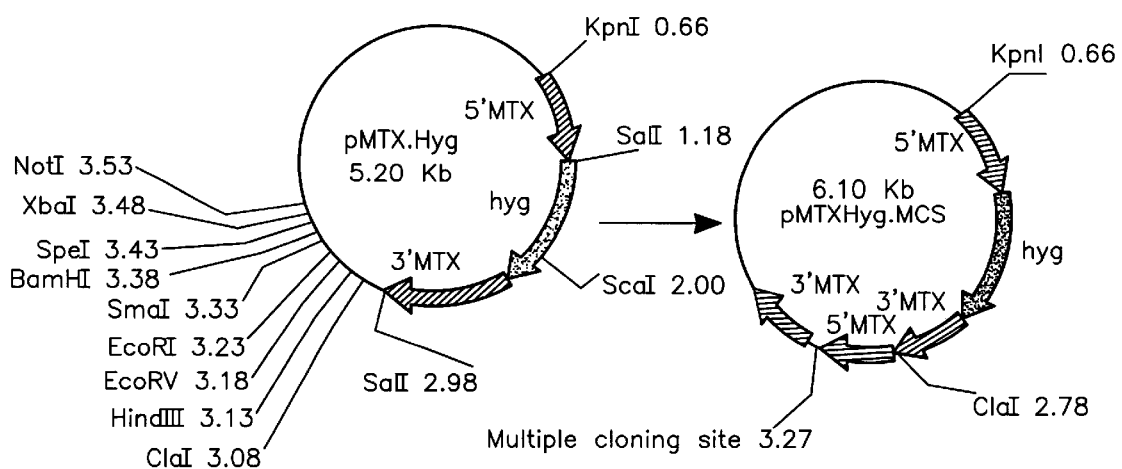
FIG. 9 depicts the expression vector pMTXHyg.MCS

The plasmid pMTXHyg.MCS (FIG. 9) is the result of modifying pMTX.Hyg to incorporate two sets of $HMTX^r$ regulatory regions, one flanking the drug resistance gene and the other flanking the multiple cloning site where genes of interest can be cloned. pMTXHyg. MCS is expected to provide higher rate of expression of foreign polypeptides in Crithidia compared to pXNeo.XGFP. The luciferase gene in pXHyg.MTX.luc is removed by digestion of pXHyg.MTX.luc with HindIII and BamHI, and a multiple cloning region is inserted in its place.

GPI-PLC assay

A pellet of $10^7$ cells was lysed in 1 ml of hypotonic buffer (10 mM $Na_2HPO_4$, 2 mM $KH_2PO_4$, 13.7 mM NaCl, 8 mM KCl, pH 7.4) containing a protease inhibitor cocktail (Garg, et al., *J. Biol. Chem.*, 272, 12482–12491 (1997)) on ice (Mensa-Wilmot, et al. *J. Cell. Biol.*, 124,935–947 (1994)). The cell suspension was incubated on ice for 30 minutes and centrifuged at 14,000 g for 15 minutes at 4° C. The cell pellet was washed with PBS (10 mM $Na_2HPO_4$, 2 mM $KH_2PO_4$, 137 mM NaCl, 8 mM KCl, pH 7.4), extracted with 100 μl of 50 mM Tris-HCl, pH 8.0, 5 mM EDTA, 1% NP40 (1×

AB) as described by Garg, et al., (J. Biol. Chem., 272, 12482–12491 (1997)). The detergent extract (1× AB extract) was assayed for GPIPLC activity using [$^3$H]myristate-labeled variant surface glycoprotein (VSG) of T. brucei as substrate (Mensa-Wilmot et al., Methods Enzymol., 250 641–655 (1995). One unit is defined as the amount of enzyme required to cleave 0.5 µg of variant surface glycoprotein.

Assay of luciferase expression

A cell extract was produced by harvesting the Crithidia at 4000×g, 2 minutes, 4° C. The cells were washed with 1×PBS once, and the number of cells determined using a hemacytometer. Luciferase activity was assayed using a luciferase assay kit (Promega, Madison, Wis.).

Results

To determine if the expression of foreign gene(s) can be obtained from pHM.Hyg or pX63.Hyg, we conducted several experiments, the results of which are shown in Table 4. First, T. brucei cDNA encoding GPI-PLC was cloned in pHM.Hyg and pX63.Hyg to generate pHMHyg.GPIPLC and pX63Hyg.GPIPLC, respectively. In repeated experiments, it was not possible to transform Crithidia with pHMHyg.GPIPLC or pX63Hyg.GPIPLC. Stable lines of Crithidia transfected with pHM.Hyg or pX63.Hyg and selected in the presence of hygromycin could be established in these same experiments suggesting that the technique of electroporation was working and that the plasmid preparations were clean for transfection (Table 2). Both pHMHyg-.GPIPLC and pX63Hyg.GPIPLC plasmids have been used successfully for the expression of GPI-PLC activity in Leishmania, indicating that the regulatory regions flanking Hyg and GPI-PLC were functional. The inability to drug select Crithidia transfectants containing pHMHyg.GPIPLC or pX63Hyg.GPIPLC therefore suggested that the expression of GPI-PLC is lethal to Crithidia. This result was not surprising because GPI-PLC cleaves GPI anchors that are used by protozoans for the attachment of a variety of proteins on the plasma membrane. Expression of GPI-PLC may have resulted in a reduction of expression of certain proteins that are essential for replication of Crithidia. Previously, this type of phenotype (i.e., the inability to express a GPI-PLC) had been observed in T. cruzi. It was also determined that there may be a 5' regulatory region contained in the 3' DHFR regulatory region of pX63,Hyg and pX63.Neo.

TABLE 4

Expression of foreign proteins in C. fasciculata

| | Plasmid | Drug | Drug Concentration (µg/ml) | Expression Obtained |
|---|---|---|---|---|
| 1. | None | None | None | NA |
| 2. | pX63.Hyg | Hyg | 100 | NA |
| 3. | pX63Hyg.GPIPLC | " | <10 | No (GPI-PLC activity assay)[1] |
| 4. | pHM.Hyg | " | 500 | NA |
| 5. | pHM.Hyg.GPIPLC | " | <10 | No (GPI-PLC activity assay)[1] |
| 6. | pMTX.Hyg. | " | 500 | NA |
| 7. | pXHyg.MTXLuc | " | <100 | No (Luciferase activity assay) |
| 8. | pSP72neo | Neo | 100 | NA |
| 9. | pSP72neo.Luc | " | 100 | No (Luciferase activity assay) |
| 10. | pX.Neo | " | <200 | NA |
| 11. | pXNeo.XGFP | " | <200 | Yes (Confocal microscopy) |
| 12. | pUTK | " | 200 | NA |
| 13. | pUTK.GPIPLC* | " | 200 | Yes (Immunoprecipitation/western blot) |

Abbreviations used: NA, Not applicable, these vectors contain drug resistance genes only.
[1]Low levels of GPI-PLC were detected at lower drug concentrations; however, since even such low levels were lethal it was not possible to select for stable, higher producing tranfectants.

The pHM.Hyg and pX63.Hyg plasmids contain one set of 5' and 3' regulatory regions for the post-transcriptional modifications and expression of a drug resistance gene. For the expression of genes lacking their own 5' and 3' regulatory regions, it was necessary to insert a second set of regulatory regions in these plasmids for the efficient expression of both drug resistance and foreign genes. Considering that pHM.Hyg (10.2 kilobases) and pX63.Hyg (6.8 kilobases) are large plasmids, it was difficult to modify these plasmids for the insertion of additional 5' and 3' regulatory regions and foreign genes. The pHM.Hyg and pX63.Hyg plasmids were therefore modified to reduce the size of 5' and 3' flanking sequences. The modified plasmids pMTX.Hyg (5.2 kilobases) and pX.Hyg (3.8 kilobases) contained ~500 base pairs (bp) of 5' regulatory region and ~800 base pairs of 3' regulatory region of HMTX$^r$ and DHFR locus, respectively. Crithidia transfected with pX.Hyg or pMTX.Hyg exhibited drug resistance similar to that shown by pX63.Hyg or pHM.Hyg transfectants (Table 2, compare rows 1, 4, 6 and 7). These results suggested that ~500 base pairs of 5' regulatory region and ~800 base pairs of 3' regulatory region is sufficient for the post-transcriptional processing and maturation of transcripts and expression of proteins.

Next, the two sets of regulatory regions were inserted in pBSK (Stratagene) such that one set could be used for the expression of a drug resistance gene and other set could be used for the expression of a foreign gene in Crithidia. First, the $Hyg^r$ gene in pMTX.Hyg was replaced with the gene encoding firefly luciferase such that the luc gene was flanked by 5' and 3' regulatory regions from the $HMTX^r$ locus of Leishmania. The luc gene and the flanking 5' and 3' regulatory regions were then cloned in pX.Hyg such that in the resulting plasmid, pXHyg.MTXLuc, the $Hyg^r$ gene was flanked by DHFR regulatory regions while luc gene was flanked by $HMTX^r$ regulatory regions.

Crithidia cells transfected with pXHyg.MTXLuc were assayed for the expression of luciferase activity. Unlike pHMHyg, pMTX.Hyg, pX63Hyg or pX.Hyg that provided significant levels of drug resistance in Crithidia transfectants, the pXHyg.MTXLuc transfectants could not be selected in the presence of high drug pressure (Table 2). In addition, luciferase activity was not detected in either transient or stable transfectants of Crithidia electroporated with pXHyg.MTXLuc. Attempts to express luc using pXHyg.MTXLuc in Leishmania and pSP72neo.luc (5', 3' flanking sequences are provided by Leishmania A2 gene locus) in Crithidia were also not successful suggesting that a mutation in the luc PCR product might be responsible for the inactivation of the luc gene. However, suppression of the $Hyg^r$ gene activity as well as luc activity in pXHyg.MTX-Luc transfectants of Crithidia or Leishmania indicated that the 3' regulatory region of luc might have an inhibitory effect on the 5' regulatory region of the $Hyg^r$ gene resulting in the inhibition of expression of $Hyg^r$ gene as well.

To circumvent the apparent inhibitory effects of regulatory regions derived from different loci on the expression of structural genes, we decided to use the regulatory regions derived from the same locus for the expression of both the $Hyg^r$ and the foreign gene in Crithidia. The pXNeo.X.GFP plasmid that contained both drug resistance and marker (green fluorescent protein, GFP) genes flanked by DHFR regulatory regions was used to transfect Crithidia to determine the expression of the drug resistance gene and the GFP. The transfectants selected in the presence of G418 (100 μg/ml) were visualized by laser scanning confocal microscopy. High-level expression of GFP in pXNeo.X.GFP transfectants could be easily detected. Controls transfected with pX.Neo were negative for the expression of GFP. These results indicate that the expression of foreign genes along with the drug selection marker can be obtained in Crithidia. It is expected that selecting the pXNeo.X.GFP transfectants at higher drug concentration will increase the level of protein expression.

pMTX.Hyg is modified to incorporate two sets of DHFR regulatory regions, and provide a vector useful for inserting a gene that is to be expressed at high level. One set of DHFR regulatory regions flanks the drug resistance gene and the other set of DHFR regulatory regions flanks the multiple cloning site where genes of interest can be cloned. pMTX-Hyg. MCS is expected to provide higher rate of expression of foreign polypeptides in Crithidia compared to pXNeo.XGFP.

EXAMPLE 3

Efficiency of Translation

The efficiency of translation of mRNAs typically depends upon the sequence and structure of the mRNA, its ribosome binding site (RBS), spacer region and translation enhancer sequences (TES). No consensus RBS, spacer or TES proximal to initiation codon have been identified in Crithidia or any other kinetoplastid. Dr. Mensa Wilmot (University of Georgia) and his research group have altered the RBS and spacer sequences of *E. coli* Lac Z gene to furnish upstream translation enhancing activity in Leishmania (Al-Qahtani et al (*Nucleic Acids Res.*, 24, 1173–1174, (1996), Teilhet et al;, *Gene*, 222, 91–97 (1998))).

Materials and Methods

Figure 4:
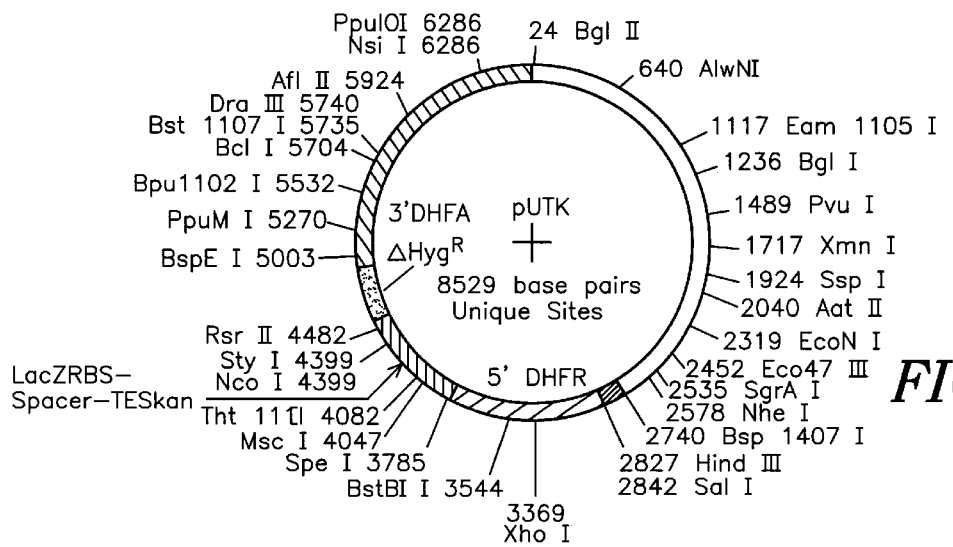
FIG. 4 depicts the expression vector pUTK

Vector construction pUTK (FIG. 4) was provided by Dr. Rashid and Dr. Mensa-Wilmot (University of Georgia). This plasmid was constructed by replacing the $Hyg^r$ gene in pX63.Hyg with LacZRBS-spacer-TES $Kan^r$ ($Kan^r$ refers to kanamycin and confers resistance to kanamycin when expressed in *E. coli* and to neomycin when expressed in Crithidia). The $Hyg^r$ gene was removed from pX63.Hyg with SacII and SpeI. The LacZRBS-spacer-TES $Kan^r$ was constructed as follows. The LacZRBS-spacer-TES $Kan^r$ was amplified by PCR using the primer pair 5' TAAGAACGTTTTCCATAACTTAGGAG-GCAGATCATGATTGAACAAGA TGGA (SEQ ID NO:7) and 5' TATGAACGTTTTCTTAGAAGAACTCGT-CAAGAAG (SEQ ID NO:8) and the kanamycin gene as template. The kanamycin gene is described in Seifert et al. (*Proc. Natl. Acad Sci. USA*, 83, 735–739 (1986)). The resulting amplified product was cloned in pBSK at the SmaI site and the resulting plasmid was designated pBSK.UTE-.$Kan^r$. The LacZRBS-spacer-TES $Kan^r$ was subcloned from pBSK.UTE.$Kan^r$ into pX63.Hyg. pX63.Hyg was digested with SacII, blunt ended, and then digested with SpeI to release the Hyg coding region and prepare the plasmid for insertion of the LacZRBS-spacer-TES $Kan^r$. The 0.8 kilobase $Kan^r$ gene along with the LacZRBS-spacer-TES at the 5' end was released from the pBSK plasmid using SpeI and EcoRV and ligated into the prepared pX63.Hyg. The resulting plasmid was designated pUTK. The LacZRBS-spacer-TES has been described by Al-Qahtani et al (*Nucleic Acids Res.*, 24, 1173–1174, (1996), and Teilhet et al., *Gene*, 222, 91–97 (1998)).

PUTK.GPIPLC* was provided by Dr. Rashid and Dr. Mensa-Wilmot (University of Georgia). This plasmid contains a cDNA encoding GPIPLC that has been mutated such that GPIPLC* lacks the enzyme activity, but can be detected using antibodies (see Rashid et al., *Eur. J. Biochem.*, 264, 914–920 (1999)). GPIPLC* was amplified by PCR using the primer pair 5' TAAGGATCCTTAACACAGGAGGCA-GACCATGTTTGGTGGTGTAAAG (SEQ ID NO:9) and 5' TAAGGATCCTTATGACCTTGCGGTTTCCTT (SEQ ID NO:10). The amplified DNA was digested with BamHII and subcloned in pUTK and the BglII site. This insertion did not disrupt the LacZRBS-spacer-TES Kan.

Assay of GPI-PLC* expression

GPI-PLC* expression was assayed as described by Armah et al., *J. Biol. Chem.*, 274, 5931–5938 (1999). Briefly, about $10^9$ Crithidia were harvested, washed and lysed in 1× lysis buffer. Cell lysate was incubated with anti-GPI-PLC antibody (polyclonal rabbit anti-GPIPLC antibody, R18B3). Antibody-GPIPLC complexes were precipitated using protein A beads. The resulting complex (antibody-GPIPLC plus protein A beads) was resolved by 10% polyacrylamide gel electrophoresis under reducing conditions, and transferred to Immobilon-P filters. Filters were then blotted with anti-GPIPLC monoclonal antibody (2A66) and alkaline phosphatase conjugated IgG. Color was developed with alkaline phosphatase substrates. Dr. Mensa-Wilmot provided the anti-GPIPLC antibody used for immuno-precipitation and western blots to detect the expression of GPIPLC* protein in Crithidia.

Results

The effect of modified Lac Z RBS-spacer-TES on the expression of foreign genes in Crithidia was determined. The PUTK.GPIPLC* vector containing Lac Z RBS-spacer-TES in front of Neo$^r$ gene and GPI-PLC* gene (GPI-PLC* lacks the enzyme activity that is lethal to Crithidia, see above) was electroporated in Crithidia. Crithidia transfected with pX63.neo was used as a control. In comparison to pX63.neo transfectants, Crithidia transformed with pUTK or PUTK.GPIPLC* were selected in the presence of high drug pressure (Table 2) and were obtained in a shorter time period. PUTK.GPIPLC* transfectants expressed GPIPLC* when assayed by immuno-precipitation and western blot.

Interestingly, PUTK.GPIPLC* conferred kanamycin resistance to E. coli as well as G418 resistance to Crithidia. Thus, PUTK.GPIPLC* was modified such that the expression of Neo$^r$ gene can be achieved across species. These results indicate that the incorporation of LacZRBS-spacer-TES sequences can enhance the expression of foreign genes along with drug resistance genes in Crithidia The Lac Z RBS-spacer-TES sequences, if required, can be incorporated by PCR at 5' end of the foreign genes to achieve high level of expression in Crithidia. The LacZRBS-spacer-TES sequence is nucleotides 10–28 of SEQ ID NO:9.

EXAMPLE 4

Protein Targeting in Crithidia

A major advantage of an expression system utilizing trypanosomatids such as Crithidia is that these organisms have a very efficient mechanism for anchoring of surface proteins via glycosylphosphatidylinositols (GPIs) and in fact use this pathway as the major mechanism for display of surface proteins. For protein expression this means that mature proteins can be targeted to the surface of the parasite and subsequently cleaved from the surface by treatment with a GPI-phospholipase or PI-phospholipase C. Thus Crithidia expressing a foreign polypeptide as a GPI anchored protein can be grown in bulk, washed to remove contaminating media components, and phospholipase-treated to obtain isolated protein. GPI-anchoring of a heterologous polypeptide (chicken ovalbumin) has been demonstrated in T. cruzi (Garg, N. et al., J. Immunol., 158, 3293–3302 (1997)). The same approach can be used for expression of heterologous proteins in Crithidia. A protein can be anchored to the Crithidia surface by a GPI anchor by adding the GPI cleavage/attachment site and carboxy terminal hydrophobic tail (amino acids 632–679) (SEQ ID NO:14) from the T. cruzi amastigote surface protein ASP-1 (Garg, N. et al., J. Immunol., 158, 3293–3302 (1997) and Santos, et al., Mol. Biochem. Parasitol., 86, 1–11 (1997)).

EXAMPLE 5

Integration of Expression Vectors in Crithidia Genomic DNA

Further optimization of a Crithidia protein expression system addresses the stable integration of plasmids into the Crithidia genome and the regulation of protein expression using a tetracycline-repressor system. The vectors used for protein expression in Crithidia are either targeted for insertion into a chromosomal site or maintained extra-chromosomally. The latter approach of plasmid expression allows for maintenance of a high copy number of the plasmid (and thus potentially higher protein production) but also requires continuous drug selection to prevent plasmid loss. Recombinants once selected do not need to be kept in the presence of continuous drug selection pressure.

Plasmids that can be inserted into a chromosomal site have been used to provide stable and efficient expression of chicken ovalbumin and luciferase in T. cruzi. Insertion of a plasmid into a chromosomal site is typically accomplished by inserting into the plasmid a nucleotide sequence that is similar or identical in sequence to a region of the chromosome. Homologous recombination can occur between these two regions and result in the integration of the plasmid into the chromosome. Portions of the alpha- or beta-tubulin genes of Crithidia are inserted into the plasmids disclosed herein to convert them into plasmids that are much more likely to integrate into the Crithidia chromosome.

EXAMPLE 6

Regulated Expression System for Expression of Toxic Genes in Crithidia

Several plasmids are required for the regulated expression system. pMTX.Hyg is modified such that the Hyg$^r$ gene is replaced by either the Neo$^r$ gene or the phleomycin resistance gene (Phleo$^r$) to result in pMTX.Neo or pMTX.Phleo.

The gene encoding T7 polymerase and the regulatory regions flanking the T. brucei aldolase gene from pHD328 (Biebinger et al., Exp. Parasitol., 83, 252–258 (1996)) are subdloned into pMTX.Hyg resulting in the construction of pMTX.Hyg.T7polymerase.

A cassette containing T7 promoter-5' regulatory region of T. brucei aldolase-Tet$^r$-3' regulatory region of T. brucei aldolase (Wirtz, E., et al., Science, 268, 1179–1183 (1995), and Wirtz et al., Nucl. Acids Res., 26, 4626–4634 (1998)) are subcloned in pMTX.Neo to construct pMTX.Neo.T7promoter-Tet$^r$.

A cassette containing T7 promoter-TetO-luc gene (Wirtz, E., et al., Science, 268, 1179–1183 (1995)) will be subdloned in pMTX.Phleo to make pMTX.Phleo.T7promoter-TetO-luc.

Crithidia sequentially transfected with these three plasmids will be selected in the presence of hygromycin, G418, and phleomycin. Transfectants will be screened for expression of luciferase in the presence or absence of tetracycline. Optionally, the 5' and 3' aldolase regulatory regions flanking the T7 polymerase, Tet$^r$ and luciferase gene will be replaced with HMTX$^r$ of DHFR regulatory regions to achieve higher expression.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for producing a polypeptide comprising:
   (a) providing a nonpathogenic protozoan host cell comprising a vector comprising a first 5' regulatory region, a first 3' regulatory region, and a first coding region located therebetween, wherein the first coding region encodes a polypeptide and is operably linked to the first 5' regulatory region and the first 3' regulatory region, and a second 5' regulatory region, a second 3' regulatory region, and a second coding region located therebetween, wherein the second coding region encodes a detectable marker and is operably linked to the second 5' regulatory region and the second 3' regulatory region; and
   (b) culturing the host cell under conditions that allow expression of the first coding region to produce the polypeptide.

2. The method of claim 1 wherein the first and second 5' regulatory region and the first and second 3' regulatory region are each derived from a protozoan.

3. The method of claim 1 wherein the second 5' regulatory region comprises a 5' regulatory region selected from the group consisting of a Leishmania H region methotrexate resistance 5' regulatory region, a Leishmania dihydrofolate reductase 5' regulatory region, and a Leishmania A2 5' regulatory region.

4. The method of claim 1 wherein the second 3' regulatory region comprises a 3' regulatory region selected from the group consisting of a Leishmania H region methotrexate resistance 3' regulatory region, a Leishmania dihydrofolate reductase 3' regulatory region, and a Leishmania A2 3' regulatory region.

5. The method of claim 1 wherein the detectable marker is a selectable marker that encodes resistance to a drug.

6. The method of claim 1 wherein the nonpathogenic protozoan is a member of the order Kinetoplastida.

7. The method of claim 1 wherein the polypeptide encoded by the first coding region comprises a signal peptide.

8. The method of claim 1 wherein the polypeptide encoded by the first coding region comprises a glycosylphosphatidylinositol (GPI) cleavage/attachment site.

9. The method of claim 1 wherein the vector is a plasmid.

10. The method of claim 1 wherein the vector is integrated into the genomic DNA of the nonpathogenic protozoan host cell.

11. The method of claim 1 wherein the vector further comprises at least a portion of one of an actin gene or a β-tubulin gene of the nonpathogenic protozoan that comprises the vector.

12. The method of claim 1 further comprising (c) isolating the polypeptide.

13. The method of claim 2 wherein the first 5' regulatory region comprises a 5' regulatory region selected from the group consisting of a Leishmania H region methotrexate resistance 5' regulatory region, a Leishmania dihydrofolate reductase 5' regulatory region, and a Leishmania A2 5' regulatory region.

14. The method of claim 2 wherein the first 3' regulatory region comprises a 3' regulatory region selected from the group consisting of a Leishmania H region methotrexate resistance 3' regulatory region, a Leishmania dihydrofolate reductase 3' regulatory region, and a Leishmania A2 3' regulatory region.

15. The method of claim 6 wherein the nonpathogenic protozoan is a Crithidia.

16. The method of claim 7 wherein the signal peptide is an amino terminal signal sequence selected from the group consisting of amino acids 1–47 of the *Trypanosoma cruzi* (*T. cruzi*) glycoprotein gp-72 (SEQ ID NO:11), amino acids 1–18 of influenza hemagglutinin (SEQ ID NO:12), and amino acids 1–22 of murine interleukin-2 (IL-2) (SEQ ID NO:13).

17. The method of claim 8 wherein the GPI cleavage/attachment site comprises amino acids 632–679 of amastigote surface protein I (SEQ ID NO:14).

18. The method of claim 9 wherein the plasmid is maintained extrachromosomally in the nonpathogenic protozoan host cell.

19. A nonpathogenic protozoan comprising a vector comprising a first coding region that encodes a polypeptide, wherein the first coding region is flanked by a first 5' regulatory region and a first 3' regulatory region, and a second coding region that encodes a detectable marker, wherein the second coding region is flanked by a second 5' regulatory region and a second 3' regulatory region.

20. The nonpathogenic protozoan of claim 19 which is a member of the order Kinetoplastida.

21. The nonpathogenic protozoan of claim 19 wherein the coding region is a heterologous coding region.

22. The nonpathogenic protozoan of claim 20 which is a Crithidia.

23. A method for producing a polypeptide comprising:
 (a) providing a nonpathogenic protozoan host cell comprising a vector comprising a 5' regulatory region, a 3' regulatory region, and a coding region located therebetween, wherein the coding region encodes a polypeptide comprising a signal peptide and is operably linked to the 5' regulatory region and the 3' regulatory region; and
 (b) culturing the host cell under conditions that allow expression of the coding region to produce the polypeptide.

24. The method of claim 23 wherein the signal peptide is an amino terminal signal sequence selected from the group consisting of amino acids 1–47 of the *T. cruzi* glycoprotein gp-72 (SEQ ID NO:11), amino acids 1–18 of influenza hemagglutinin (SEQ ID NO:12), and amino acids 1–22 of murine IL-2 (SEQ ID NO:13).

25. A method for producing a polypeptide comprising:
 (a) providing a nonpathogenic protozoan host cell comprising a vector comprising a 5' regulatory region, a 3' regulatory region, and a coding region located therebetween, wherein the coding region encodes a polypeptide and is operably linked to the 5' regulatory region and the 3' regulatory region, and wherein the polypeptide comprises a GPI cleavage/attachment site comprising amino acids 632–679 of amastigote surface protein I (SEQ ID NO:14); and
 (b) culturing the host cell under conditions that allow expression of the coding region to produce the polypeptide.

26. A vector comprising a 5' regulatory region, a 3' regulatory region, and a coding region located therebetween, wherein the coding region encodes a polypeptide comprising a signal peptide and is operably linked to the 5' regulatory region and the 3' regulatory region, and wherein the 5' regulatory region and the 3' regulatory regions are each derived from a protozoan.

27. A vector comprising a 5' regulatory region, a 3' regulatory region, and a coding region located therebetween, wherein the coding region encodes a polypeptide comprising a signal peptide and is operably linked to the 5' regulatory region and the 3' regulatory region, wherein the signal peptide is an amino terminal signal peptide selected from the group consisting of amino acids 1–47 of the *T. cruzi* glycoprotein gp-72 (SEQ ID NO:11) and amino acids 1–18 of influenza hemagglutinin (SEQ ID NO:12).

28. A vector comprising a 5' regulatory region, a 3' regulatory region, and a coding region located therebetween, wherein the coding region encodes a polypeptide comprising a GPI cleavage/attachment site comprising amino acids 632–679 of amastigote surface protein I (SEQ ID NO:14), and the coding region is operably linked to the 5' regulatory region and the 3' regulatory region.

29. A vector comprising a first 5' regulatory region, a first 3' regulatory region, and a first coding region located therebetween, wherein the coding region encodes a polypeptide and is operably linked to the first 5' regulatory region and the first 3' regulatory region, and a second 5' regulatory region, a second 3' regulatory region, and a second coding region located therebetween, wherein the second coding region encodes a detectable marker and is operably linked to the second 5' regulatory region and the second 3' regulatory region, wherein the first and second 5' regulatory regions and the first and second 3' regulatory regions are each derived from a protozoan.

30. The vector of claim 29 wherein the first 5' regulatory region comprises a 5' regulatory region selected from the group consisting of a Leishmania H region methotrexate resistance 5' regulatory region, a Leishmania dihydrofolate reductase 5' regulatory region, and a Leishmania A2 5' regulatory region.

31. The vector of claim 29 wherein the second 5' regulatory region comprises a 5' regulatory region selected from the group consisting of a Leishmania H region methotrexate resistance 5' regulatory region, a Leishmania dihydrofolate reductase 5' regulatory region, and a Leishmania A2 5' regulatory region.

32. The vector of claim 29 wherein the first 3' regulatory region comprises a 3' regulatory region selected from the group consisting of a Leishmania H region methotrexate resistance 3' regulatory region, a Leishmania dihydrofolate reductase 3' regulatory region, and a Leishmania A2 3' regulatory region.

33. The vector of claim 29 wherein the second 3' regulatory region comprises a 3' regulatory region selected from the group consisting of a Leishmania H region methotrexate resistance 3' regulatory region, a Leishmania dihydrofolate reductase 3' regulatory region, and a Leishmania A2 3' regulatory region.

34. The vector of claim 29 wherein the first 5' regulatory region and the first 3' regulatory region are from the same gene, and the second 5' regulatory region and the second 3' regulatory region are from the same gene.

35. The vector of claim 34 wherein the first 5' regulatory region and the first 3' regulatory region and the second 5' regulatory region and the second 3' regulatory region are from the same gene.

36. A vector comprising a first 5' regulatory region, a first 3' regulatory region, and a first coding region located therebetween, wherein the coding region encodes a polypeptide and is operably linked to the first 5' regulatory region and the first 3' regulatory region, and a second 5' regulatory region, a second 3' regulatory region, and a second coding region located therebetween, wherein the second coding region encodes a detectable marker and is operably linked to the second 5' regulatory region and the second 3' regulatory region, wherein the second 5' regulatory region and the second 3' regulatory region are each derived from a protozoan.

37. A vector comprising a first 5' regulatory region, a first 3' regulatory region, and a first coding region located therebetween, wherein the coding region encodes a polypeptide and is operably linked to the first 5' regulatory region and the first 3' regulatory region, and a second 5' regulatory region, a second 3' regulatory region, and a second coding region located therebetween, wherein the second coding region encodes a detectable marker and is operably linked to the second 5' regulatory region and the second 3' regulatory region, wherein the polypeptide comprises a signal peptide.

38. The vector of claim 37 wherein the signal peptide is an amino terminal signal peptide selected from the group consisting of amino acids 1–47 of the T. cruzi glycoprotein gp-72 (SEQ ID NO:11), amino acids 1–18 of influenza hemagglutinin (SEQ ID NO:12), and amino acids 1–22 of murine IL-2 (SEQ ID NO:13).

39. A vector comprising a first 5' regulatory region, a first 3' regulatory region, and a first coding region located therebetween, wherein the coding region encodes a polypeptide and is operably linked to the first 5' regulatory region and the first 3' regulatory region, and a second 5' regulatory region, a second 3' regulatory region, and a second coding region located therebetween, wherein the second coding region encodes a detectable marker and is operably linked to the second 5' regulatory region and the second 3' regulatory region, wherein the polypeptide comprises a GPI cleavage/attachment site.

40. The vector of claim 39 wherein the GPI cleavage/attachment site comprises amino acids 632–679 of amastigote surface protein I (SEQ ID NO:14).

41. A vector comprising a first 5' regulatory region, a first 3' regulatory region, and a first coding region located therebetween, wherein the coding region encodes a polypeptide and is operably linked to the first 5' regulatory region and the first 3' regulatory region, and a second 5' regulatory region, a second 3' regulatory region, and a second coding region located therebetween, wherein the second coding region encodes a detectable marker and is operably linked to the second 5' regulatory region and the second 3' regulatory region, wherein the first and second 5' regulatory regions each comprise a Leishmania DHFR 5' regulatory region and the first and second 3' regulatory regions each comprise a Leishmania DHFR 3' regulatory region.

42. A nonpathogenic protozoan comprising a vector comprising a coding region that encodes a polypeptide, wherein the coding region is flanked by a 5' regulatory region and a 3' regulatory region, wherein the 5' regulatory region is selected from the group consisting of a Leishmania HMTX$^r$ 5' regulatory region, a Leishmania DHFR 5' regulatory region, and a Leishmania A2 5' regulatory region, and wherein the 3' regulatory region is selected from the group consisting of a Leishmania HMTX$^r$ 3' regulatory region, a Leishmania DHFR 3' regulatory region, and a Leishmania A2 3' regulatory region, and wherein the nonpathogenic protozoan is selected from the group consisting of nonpathogenic members of the genus Trypanosoma, members of the genus Blastocrithidia, members of the genus Herpetomonas, members of the genus Leptomonas, members of the genus Phytomonas, members of the genus Crithidia, and *Leishmania chamaelonis*.

* * * * *

UNITED STATES PATENT AND TRADEMARK OFFICE
CERTIFICATE OF CORRECTION

PATENT NO. : 6,368,827 B1
DATED : April 9, 2002
INVENTOR(S) : Tarleton et al.

It is certified that error appears in the above-identified patent and that said Letters Patent is hereby corrected as shown below:

Title page,
Item [56], References Cited, please add a "FOREIGN PATENT DOCUMENTS", and insert -- EP 0 829 540 A   03/18/98   Europe --;
Item [56], References Cited, OTHER PUBLICATIONS, in the "Udenfriend et al.," reference, please delete "Glycosylphosphatidylinosito-1--Anchored" and insert -- Glycosylphosphatidylinositol--Anchored --;

Column 31,
Line 21, after "wherein the", please insert -- first --.

Signed and Sealed this

Fifth Day of November, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

PATENT NO. : 6,368,827 B1
DATED : April 9, 2002
INVENTOR(S) : Tarleton et al.

It is certified that error appears in the above-identified patent and that said Letters Patent is hereby corrected as shown below:

<u>Title page,</u>
Item [56], References Cited, please add FOREIGN PATENT DOCUMENTS, and insert -- EP 0 829 540 A  03/18/98  Europe --;
Item [56], References Cited, OTHER PUBLICATIONS, in the "Udenfriend et al.," reference, please delete "Glycosylphosphatidylinosito-1--Anchored" and insert -- Glycosylphosphatidylinositol--Anchored --;

<u>Column 31,</u>
Line 21, after "wherein the", please insert -- first --.

Signed and Sealed this

Twelfth Day of November, 2002

Attest:

Attesting Officer

JAMES E. ROGAN
*Director of the United States Patent and Trademark Office*